US011136626B2

(12) United States Patent
Sharp et al.

(10) Patent No.: US 11,136,626 B2
(45) Date of Patent: Oct. 5, 2021

(54) BIOMARKERS FOR THE DIAGNOSIS OF LACUNAR STROKE

(71) Applicant: The Regents of the University of California, Oakland, CA (US)

(72) Inventors: Frank Sharp, Davis, CA (US); Glen C. Jickling, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/228,030

(22) Filed: Dec. 20, 2018

(65) Prior Publication Data
US 2019/0390276 A1    Dec. 26, 2019

Related U.S. Application Data

(60) Continuation of application No. 15/091,181, filed on Apr. 5, 2016, now Pat. No. 10,196,690, which is a division of application No. 13/410,025, filed on Mar. 1, 2012, now abandoned.

(51) Int. Cl.
| | | |
|---|---|---|
| *C12Q 1/6883* | (2018.01) | |
| *G01N 33/68* | (2006.01) | |
| *C40B 40/06* | (2006.01) | |

(52) U.S. Cl.
CPC ....... *C12Q 1/6883* (2013.01); *G01N 33/6893* (2013.01); *C12Q 2600/112* (2013.01); *C12Q 2600/158* (2013.01); *C40B 40/06* (2013.01); *G01N 2800/2871* (2013.01)

(58) Field of Classification Search
None
See application file for complete search history.

(56) References Cited

U.S. PATENT DOCUMENTS

| | | |
|---|---|---|
| 9,057,109 B2 | 6/2015 | Chang |
| 9,200,322 B2 | 12/2015 | Barr et al. |
| 9,410,204 B2 | 8/2016 | Sharp et al. |
| 9,803,243 B2 | 10/2017 | Sharp et al. |
| 10,017,821 B2 | 7/2018 | Sharp et al. |
| 10,047,396 B2 | 8/2018 | Sharp et al. |
| 10,196,690 B2 | 2/2019 | Sharp et al. |
| 2001/0053519 A1 | 12/2001 | Fodor et al. |
| 2002/0115120 A1 | 8/2002 | Kapeller-Libermann et al. |
| 2003/0119064 A1 | 6/2003 | Valkirs et al. |
| 2003/0199000 A1 | 10/2003 | Valkirs et al. |
| 2004/0191783 A1 | 9/2004 | Leclercq et al. |
| 2004/0203083 A1 | 10/2004 | Buechler |
| 2006/0046259 A1 | 3/2006 | Baird et al. |
| 2006/0078882 A1 | 4/2006 | Zetter et al. |
| 2007/0042425 A1 | 2/2007 | Hochstrasser et al. |
| 2007/0050146 A1 | 3/2007 | Bentwich et al. |
| 2007/0280917 A1 | 12/2007 | Helgadottir |
| 2009/0148933 A1 | 6/2009 | Battrell et al. |
| 2009/0197774 A1 | 8/2009 | Kozian et al. |
| 2010/0105046 A1 | 4/2010 | Epstein et al. |
| 2010/0197518 A1 | 8/2010 | Xu et al. |
| 2010/0216115 A1 | 8/2010 | Yan et al. |
| 2012/0015904 A1 | 1/2012 | Sharp et al. |
| 2012/0065087 A1 | 3/2012 | Sharp et al. |
| 2012/0316076 A1 | 12/2012 | Sharp et al. |
| 2015/0018234 A1 | 1/2015 | Sharp et al. |
| 2016/0222455 A1 | 8/2016 | Xu et al. |
| 2016/0237501 A1 | 8/2016 | Sharp et al. |
| 2016/0265059 A1 | 9/2016 | Sharp et al. |
| 2017/0029891 A1 | 2/2017 | Sharp et al. |

FOREIGN PATENT DOCUMENTS

| | | |
|---|---|---|
| WO | 02/12892 A2 | 2/2002 |
| WO | 03/016910 A1 | 2/2003 |
| WO | 2005/116268 A2 | 12/2005 |
| WO | 2006/036220 A2 | 4/2006 |
| WO | 2008/137465 A1 | 11/2008 |
| WO | 2010/012834 A1 | 2/2010 |
| WO | 2012/009547 A2 | 1/2012 |
| WO | 2012/009567 A2 | 1/2012 |
| WO | 2012/121978 A2 | 9/2012 |
| WO | 2013/103781 A1 | 7/2013 |

OTHER PUBLICATIONS

Hassan et al., "Markers of endothelial dysfunction in lacunar infarction and ischaemic leukoaraiosis," Brain 2003, 126:424-432. (Year: 2003).*
Davi et al., "CD40 Ligand and MCP-1 as Predictors of Cardiovascular Events in Diabetic Patients with Stroke," J. Atheroscler. Thromb. 2009, 16:707-713. (Year: 2009).*
Barr et al., "Genomic biomarkers and cellular pathways of ischemic stroke by RNA gene expression profiling," Neurology 2010, 75: 1009-1014. (Year: 2010).*
Jickling et al., "Profiles of Lacunar and Nonlacunar Stroke," Ann. Neurol. 2011,70:477-485. (Year: 2011).*
Cheung et al., "Natural variation in human gene expression assessed in lymphoblastoid cells," Nature Genetics 2003, 33:422-425. (Year: 2003).*
Thellin et al., "Housekeeping genes as internal standards: use and limits," J. Biotechnol. 1999, 75:291-295. (Year: 1999).*
Haller et al., "Equivalence test in quantitative reverse transcription polymerase chain reaction: confirmation of reference genes suitable for normalization," Anal. Biochem. 2004, 335:1-9. (Year: 2004).*
Adams et al., "Classification of Subtype of Acute Ischemic Stroke", Definitions for Use in a Multicenter Clinical Trial, vol. 24, No. 1, Jan. 1993, pp. 35-41.
Saito-Hisaminato et al., "Genome-Wide Profiling of Gene Expressing in 29 Normal Human Tissues with a cDNA Microarray", DNA Research, vol. 9, Issue 2, Apr. 30, 2002, pp. 35-45.

(Continued)

*Primary Examiner* — Kaijiang Zhang

(74) *Attorney, Agent, or Firm* — Kilpatrick Townsend & Stockton LLP

(57) ABSTRACT

This invention provides gene expression profiles useful for diagnosing lacunar stroke and for distinguishing lacunar stroke from non-lacunar stroke.

16 Claims, 4 Drawing Sheets

(56) References Cited

OTHER PUBLICATIONS

"*Homo sapiens* disabled homolog 2, mitogen-responsive phosphoprotein (Drosophila), mRNA (cDNA clone MGC:1764 Image:3504380), complete cds ," Accession: BC003064.2, GI: 33870637, [Downloaded on Feb. 21, 2017 at https://www.ncbi.nlm.nih.gov/nuccore/BC003064.2?report-girevhist], 1 page.

"Affymetrix GeneChip Human Genome U133 Array Set HG-U133B," *GEO Accession viewer* (Mar. 11, 2002), XP002427171 pp. 1-4.

"Affymetrix Genechip Human Genome U133 plus 2.0 Array," *GEO Accession viewer* 7 (Nov. 7, 2003), XP002343693 pp. 1-3.

Barr et al. (2010) "Genomic biomarkers and cellular pathways of ischemic stroke by RNA gene expression profiling" *Neurology* 75:1009-1014.

Benner et al. (2001) "Evolution, language and analogy in functional genomics," *Trends in Genetics* 17(7):414-418.

BETSI Project, Biotechnology Education & Training Sequence Investment, (2008) "Preparation of Human Chromosome Spreads," 6 pages; Southwestern College, 900 Otay Lakes Road, Chula Vista, 91910, www.swccd.edu/-betsi.

Cheung et al. (2003) "Natural variation in human gene expression assessed in lymphoblastoid cells," *Nature Genetics* 33:422-425.

Cobb et al. (2002) "Sepsis gene expression profiling: Murine splenic compared with hepatic responses determined by using complementary DNA microarrays," *Crit Care Med* 30(12):2711-2721.

Crawford et al., (2007) "The biological importance of measuring individual variation," *J. Exp. Biol.* 210:1613-1621.

Davi et al. (2009) "CD40 ligand and MCP-1 as predictors of cardiovascular events in diabetic patients with stroke," *J. Atheroscler. Thromb.* 16:707-713.

European Extended Search Report dated Apr. 11, 2014 issued in EP 11 807 519.1.

European Extended Search Report dated Mar. 16, 2011 issued in EP 10014221.5.

European Extended Search Report dated Nov. 12, 2013 issued in EP11807532.4.

Ferronato et al. (2010) "Upregulated Expression of Toll-like Receptor 4 in Peripheral Blood of Ischaemic Stroke Patients Correlates with Cyclooxygenase 2 Expression," *European Journal of Vascular and Endovascular Surgery* 41(3): 358-363.

Fung et al. (2008) "A biomarker panel for peripheral arterial disease," *Vasc. Med.* 13:217-224.

Greenbaum et al. (2003) "Comparing protein abundance and mRNA expression levels on a genomic scale," *Genome Biology* 4:117(1-8).

Haller et al. (2004) "Equivalence test in quantitative reverse transcription polymerase chain reaction: confirmation of reference genes suitable for normalization," *Anal. Biochem.* 335:1-9.

Hassan et al. (2003) "Marker of endothelial dysfunction in lacunar infarction and ischaemic leukoaraiosis," *Brain* 126:424-432.

Howell et al. "Differential staining of the satellite regions of human acrocentric chromosomes," Experientia, Feb. 1975, vol. 31, No. 2, pp. 260-262. <doi:https://doi.org/10.1007/BF01990741>.

Jakobsen et al. (1990) "Purification of mRNA directly from crude plant tissues in 15 minutes using magnetic oligo dT microspheres," *Nucleic Acids Research*, 18(12):3669.

Jensen et al. (2008) "The promise and potential pitfalls of serum biomarkers for ischemic stroke and transient ischemic attack," *Neurologist* 14(4):243-246.

Jensen et al. (2009) "Potential biomarkers for the diagnosis of stroke," Expert Review of Cardiovascular Therapy, 7(4):389-93.

Jickling et al. (2010) "Biomarkers of ischemic stroke," US Neurology, 5(2):52-54.

Jickling et al. (2011) "Profiles of lacunar and non-lacunar stroke," Ann Neurol., 70(3):477-485.

Jickling et al. (2012) "Prediction of cardioembolic, arterial and lacunar causes of cryptogenic stroke by gene expression and infarct location," Stroke, 43(8): 2036-2041 [doi:10.1161/STROKEAHA. 111.648725 pp. 1-12].

Jickling et al. (Nov. 2010) "Signatures of cardioembolic and large vessel ischemic stroke," Ann Neurol., 68(5):681-692.

Karl-Olof Lövblad et al. (2006) "Actual diagnostic approach to the acute stroke patient," Neuro Eur Radiol, 16:1253-1269.

Laskowitz et al. (2005) "Panel of Biomarkers Predicts Stroke," Ann. N.Y. Acad. Sci., 1053:30.

Leypoldt et al. (2009) "Dimethylarginine Dimethylaminohydrolase-1 Transgenic Mice are not Protected from Ischemic Stroke," PlosOne, 4(10):e7337(1-4).

Li et al. (Oct. 2013) "Transcriptome Analysis Reveals Distinct Patterns of Long Noncoding RNAs in Heart and Plasma of Mice with Heart Failure," PLOS ONE, 8(10):e77938, 10 pp.

Lim et al. (2010) "MicroRNA in Cerebral Ischemia," Translational Stroke Research, 1:287-303.

Lynch et al. (2004) "Novel diagnostic test for acute stroke," Stroke, 35(1):57-63.

May et al. (1988) "How many species are there on Earth," Science, 241:1441-1449.

Montaner et al. (2008) "Etiologic diagnosis of ischemic stroke subtypes with plasma biomarkers," Stroke, 39(8):2280-2287.

Moore et al. (2005) "Using peripheral blood mononuclear cells to determine a gene expression profile of acute ischemic stroke: a pilot investigation," Circulation, 111(2):212-21.

Patel et al. (Dec. 12, 2001) "Lack of Clinical Significance of Early Ischemic Changes on Computed Tomography in Acute Stroke," Jama, 286(22):2830-2838.

PCT International Preliminary Report on Patentability dated Jan. 15, 2013 issued in PCT/US2011/044023.

PCT International Preliminary Report on Patentability dated Jan. 15, 2013 issued in PCT/US2011/044062.

PCT International Preliminary Report on Patentability dated Jul. 8, 2014 issued in PCT/US2013/020240.

PCT International Preliminary Report on Patentability dated Nov. 3, 2009 issued in PCT/US2008/062064.

PCT International Preliminary Report on Patentability dated Sep. 10, 2013 issued in PCT/US2012/027316.

PCT International Search Report and Written Opinion dated Apr. 12, 2013 issued in PCT/US2013/020240.

PCT International Search Report and Written Opinion dated Jul. 25, 2008 issued in PCT/US2008/062064.

PCT International Search Report and Written Opinion dated Mar. 28, 2012 issued in PCT/US2011/044023.

PCT International Search Report and Written Opinion dated Mar. 28, 2012 issued in PCT/US2011/044062.

PCT International Search Report and Written Opinion dated Oct. 24, 2012 issued in PCT/US2012/027316.

Pradervand et al. (2008) "Affymetrix Whole-Transcript Human Gene 1.0 ST array is highly concordant with standard 3'expression arrays," BioTechniques, 44(6):759-762.

Read et al. (2001) "Stroke Genomics: Approaches to Identify, Validate, and Understand Ischemic Stroke Gene Expression," J. Cereb. Blood Flow Metab., 21:755-778.

Reynolds et al. (2003) "Early Biomarkers of Stroke," Clin. Chem., 49:1733-1739.

Rothwell et al. (2007) "Effect of urgent treatment of transient ischaemic attack and minor stroke on early recurrent stroke (Express study): a prospective population-based sequential comparison," Lancet, 370:1432-42.

Sendera et al. (2002) "Expression Profiling with Oligonucleotide Arrays: Technologies and Applications for Neurobiology," Neurochemical Research, 27:1005-1026.

Sharp et al. (2007) "Genomic Profiles of Stroke in Blood," Stroke, 28:691-693.

Shendure et al. (Oct. 2008) "Next-generation DNA sequencing," Nature Biotechnology, 26(10):1135-1145.

Slogoff et al.(1985) "Does Perioperative Myocardial Ischemia Lead to Postoperative Myocardial Infarction?" Anesthesiology, 62:107-114.

Stamova et al. (2009) "Identification and validation of suitable endogenous reference genes for gene expression studies in human peripheral blood," BMC Medical Genomics 2:49 pages, 1-13.

Stamova et al. (2010) "Gene Expression Profiling of Blood for the Prediction of Ischemic Stroke," Supplementary Material, Stroke, 41(10):2171-2177, 26 pages.

(56) References Cited

OTHER PUBLICATIONS

Stapleton et al. (Mar. 1999) "Prospective Comparison of Whole-Blood- and Plasma-Based Hepatitis C Virus RNA Detection Systems: Improved Detection Using Whole Blood as the Source of Viral RNA," Journal of Clinical Microbiology, 37(3):484-489.

Swarup et al. (2007) "Circulating (cell-free) nucleic acids—a promising, non-invasive tool for early detection of several human diseases," FEBS Letters, 581:795-799.

Tang et al. (2005) "Blood Gene Expression Profiling of Neurologic Diseases: a Pilot Microarray Study," Arch Neurol., 62:210-215.

Tang et al.(2006) "Gene expression in blood changes rapidly in neutrophils and monocytes after ischemic stroke in humans: a microarray study," Journal of Cerebral Blood Flow and Metabolism, 26(8):1089-1102.

Thellin et al. (1999) "Housekeeping genes as internal standards: use and limits," J. Biotechnol., 75:291-295.

Tombul et al. (2005) "Hemostatic markers and platelet aggregation factors as predictive markers for type of stroke and neurological disability following cerebral infarction," Journal of Clinical Neuroscience, 12(4): 429-434.

Veltkamp et al. (2002) "Transient focal ischemia increases endothelial nitric oxide synthase in cerebral blood vessels," Stroke, 33(11):2704-2710.

Viswanathan et al. (2006) "Cerebral Microhemorrhage," Stroke, Journal of the American Heart Association, 37:550-555.

Whiteley et al. (2008) "Blood Biomarkers in the Diagnosis of Ischemic Stroke: A Systematic Review," Stroke, 39(10):2902-2909.

Whiteley et al. (2009) "Blood Markers for the Prognosis of Ischemic Stroke: A Systematic Review," Stroke, 40:e380-e389, 27 pages.

Xu et al. (2008) "Gene expression in peripheral blood differs after cardioembolic compared with large-vessel atherosclerotic stroke: biomarkers for the etiology of ischemic stroke," J Cereb Blood Flow Metab., 28(7):1320-1328 [Epub Apr. 2, 2008].

Zhan et al. (2010) "Brief focal cerebral ischemia that simulates transient ischemic attacks in humans regulates gene expression in rat peripheral blood" J Cereb Blood Flow & Metab., 30(1):110-118 [DOI: 10.1038/jcbfm.2009.189].

Zhan et al. (2011) "Transient ischemic attacks characterized by RNA profiles in blood," Neurology, 77(19):1718-1724.

Ziegler et al. (2007) "TLR2 has a Detrimental role in Mouse Transient Focal Cerebral Ischemia," Biochemical and Biophysical Research Communication, 359:574-579.

Adams et al., "Update to the AHA/ASA Recommendations for the Prevention of Stroke in Patients With Stroke and Transient Ischemic Attack", Stroke, vol. 39, No. 5, May 2008, pp. 1647-1652.

Hou et al., "High-Density DNA Microarray Analysis of Gene Expression Following Transient Focal Cerebral Ischemia in Mouse", International Congress Series, vol. 1252, Jun. 2003, pp. 45-56.

Schneck, "Cardioembolic Stroke", Medscape, Available online at https://emedicine.medscape.com/article/1160370-overview, 2015, 19 pages.

Zhao et al., "Differentially Expressed Genes in Asbestos-Induced Tumorigenic Human Bronchial Epithelial Cells: Implication for Mechanism", Carcinogenesis, vol. 21, Issue 11, Nov. 2000, pp. 2005-2010.

\* cited by examiner

Fig. 1A-B

FIG. A
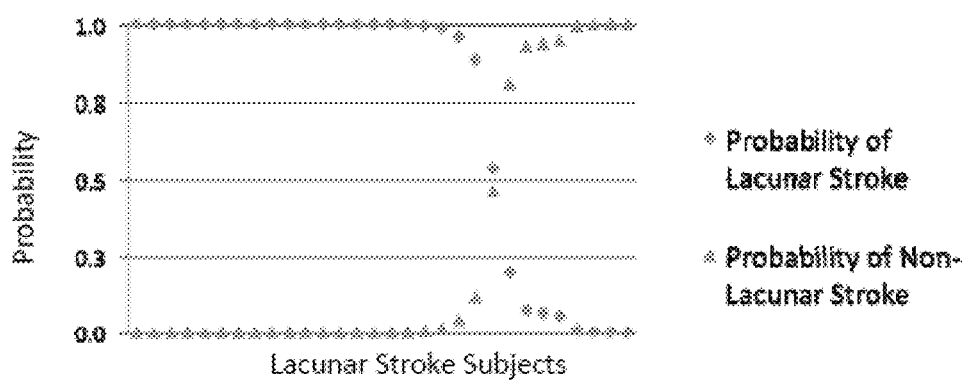
FIG. B
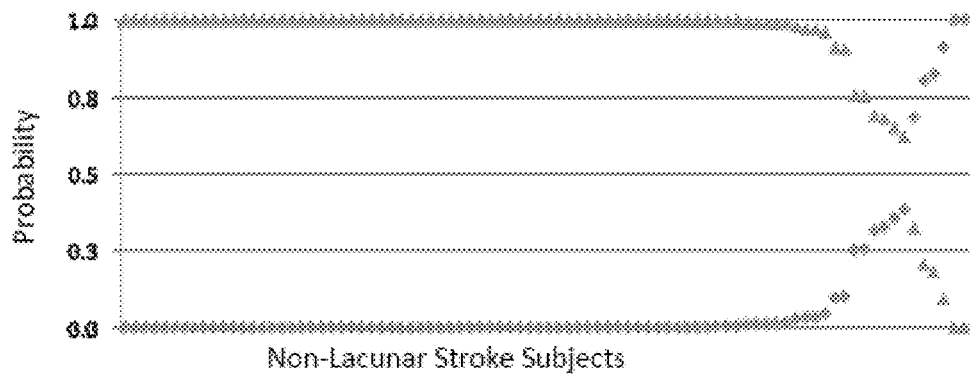
Fig. 4A-B

BIOMARKERS FOR THE DIAGNOSIS OF LACUNAR STROKE

CROSS-REFERENCE TO RELATED APPLICATIONS

This application is a continuation of U.S. application Ser. No. 15/091,181, filed Apr. 5, 2016, which is a divisional of U.S. application Ser. No. 13/410,025, filed on Mar. 1, 2012, which claims the benefit of U.S. Provisional Application No. 61/449,347, filed on Mar. 4, 2011, which are hereby incorporated herein in their entireties for all purposes.

STATEMENT OF GOVERNMENTAL SUPPORT

This work was supported in part by Grant No NS056302, awarded by the National Institutes of Health and National Institute of Neurological Disorders and Stroke (NINDS). The Government has certain rights in this invention.

FIELD OF THE INVENTION

The present invention relates to expression profiling to differentiate stroke of lacunar etiology from non-lacunar stroke.

BACKGROUND OF THE INVENTION

Small deep infarcts (SDI) including lacunar stroke account for greater than one quarter of all ischemic strokes. Though SDI cause the smallest amount of brain injury of all stroke subtypes, long-term outcomes are significant with 42% of lacunar stroke patients being dependent by 3 years (Samuelsson et al., *Stroke* (1996) 27(5):842-6; Lee, et al., *Int J Cardiol.* (2009) Mar. 25; Giroud, et al, *Rev Neurol* (Paris). (1991) 147(8-9):566-72; Clavier, et al., *Stroke.* (1994) 25(10):2005-9; Carod-Artal, et al., *Stroke.* (2005) 36(5):965-70). Indeed, lacunar strokes are indicative of cardiovascular disease with an annual death rate of 2.8% and an increased risk of recurrent stroke, white matter disease and cognitive impairment (Samuelsson, et al., supra; Norrving, *Lancet Neurol.* (2003) 2(4):238-45; Jackson, et al., *Brain.* (2005) 128(Pt 11):2507-17).

The term lacune was first used to describe small subcortical infarctions in the 1800s by Dechambre and Durand-Fardel. In the 1960s Miller Fisher described the lacunar hypothesis, correlating the clinical symptoms of lacunar syndromes with pathologic findings of single perforating branch occlusion from microatheroma or lipohyalinosis (Fisher, *Acta Neuropathol.* (1968) 12(1):1-15; Fisher, *Neurology* (1965) 15:774-84; Fisher, *Neurology* (1982) 32(8): 871-6; and Bamford and Warlow, *Stroke.* (1988) 19(9):1074-82). The lacunar hypothesis distinguishes lacunar stroke from other causes of SDI, including disease of the parent artery and embolism of arterial or cardiac origin. Determining whether an SDI is of small vessel lacunar or non-small vessel etiology remains a topic of controversy and investigation (Millikan, et al., *Stroke* (1990) 21(9):1251-7; Futrell, *Stroke* (2004) 35(7):1778-9; Norrving, *Stroke* (2004) 35(7): 1779-80; Davis and Donnan, *Stroke* (2004) 35(7):1780-1; and Maron, et al., *J Am Coll Cardiol.* (2002) 39(2):301-7). An embolic cause of stroke warrants a different investigative strategy and treatment than other ischemic stroke syndromes. In particular, it is important to diagnose disease that would change management, such as carotid surgery for symptomatic carotid stenosis and warfarin for symptomatic atrial fibrillation. Therefore, ascertaining the etiology of SDI is not only of academic interest but also of clinical significance.

The presence of a potential cardioembolic or arterial embolic source does not necessarily imply a causal association with SDI. Indeed, most of the vascular risk factors associated with lacunar infarction are also those that predispose to arterial and cardioembolic disease. Several predictors have been identified to suggest an SDI is of lacunar etiology. The clinical features of a lacunar syndrome predict infarcts that are radiological findings consistent with lacunar stroke (Gan, et al., *Neurology* (1997) 48(5):1204-11; and Lee, et al., *Stroke* (2005) 36(12):2583-8). However, lacunar syndromes can be mimicked by non-lacunar disease, such as cortical infarction, hemorrhagic stroke and non-vascular disease (Wessels, et al., *Stroke* (2005) 36(4):757-61; Arboix, et al., *BMC Neurol.* (2010) 10:31). Furthermore, infarction in the regions of the penetrating arteries (basal ganglia, thalamus, internal capsule, corona radiata and pons) can result from non-lacunar disease, including disease of the parent artery and emboli of arterial or cardiac origin. Infarct diameter <15 mm is also predictive of lacunar stroke, since this is the approximate vascular territory of a single penetrating artery (Bang, et al., *Cerebrovasc Dis.* (2007) 24(6): 520-9; Cho, et al., *Cerebrovasc Dis.* (2007) 23(1):14-9; and Lodder, *Cerebrovasc Dis.* (2007) 24(1):156-7). However, in patients with SDI >15 mm in size or with a coincidental arterial or cardioembolic source, it remains less clear as to whether a stroke is of lacunar or non-lacunar etiology.

The present invention is based, in part, on using gene expression profiling to distinguish patients who have suffered or are at risk of suffering lacunar stroke from patients who have suffered or are at risk of suffering embolic strokes using a gene expression profiling. The gene expression profiles further find use to predict the cause of stroke in SDI of unclear cause (SDI size >15 mm or SDI with potential embolic source). It has recently been demonstrated that cardioembolic and large vessel causes of stroke have unique gene expression signatures (Jickling, et al., *Ann Neurol.* (2010) 68(5):681-92; and Xu, et al., *J Cereb Blood Flow Metab.* (2008) 28(7):1320-8). These signatures can be used to categorize, diagnose and treat stroke patients by cause based on a profile of differentially expressed genes. The identified genes were predominantly expressed in inflammatory cells associated with each stroke subtype. The present invention is based, in part, on the identification of a profile of differentially expressed genes useful to distinguish lacunar stroke from non-lacunar stroke and to predict etiology in SDI of unclear cause.

SUMMARY OF THE INVENTION

The present invention provides biomarker useful for diagnosing the occurrence or risk of lacunar stroke and for distinguishing the occurrence or risk of lacunar stroke from non-lacunar stroke. Accordingly, in one aspect, the invention provides methods for diagnosing the occurrence of lacunar stroke or a predisposition for experiencing lacunar stroke. In some embodiments, the methods comprise:

a) determining a level of expression of a plurality of lacunar stroke-associated biomarkers in a biological sample from a patient, wherein the biomarkers are selected from Table 3; and b) comparing the level of expression of the lacunar stroke-associated biomarkers to the expression level of a plurality of stably expressed endogenous reference biomarkers;

wherein an increase of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3, CCDC114, AKAP9, BNC2, BZRAP1, CCL4, CHST2, CSF1, ERBB2, GBR56, GRAMD3, GRHL2, GRK4, ITIH4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, and ZNF827, and/or a decrease of the expression level of one or more biomarkers selected from the group consisting of HLA-DQA1, FLJ13773, QKI, MPZL3, FAM70B, LOC254128, IL8, CHML, STX7, VAPA, UGCG, PDXDC1, LRRC8B, STK4, GTF2H2, AGFG1, BTG1, CFDP1, CNPY2, FAM105A, GATM, GTF2H2B, IGHG1, IL18RAP, N4BP2, PHACTR1, RTKN2, SLC16A1, SOCS1, SPAG17, ST6GALNAC1, STK17B, STT3B, STX16, TBC1D12, TRIM4, UACA, and WHAMML2 compared to the expression level of the plurality of endogenous reference biomarkers is correlative with or indicates that the patient suffers from or is at risk of experiencing lacunar stroke, thereby diagnosing the occurrence of lacunar stroke or the predisposition for experiencing lacunar stroke.

In a related aspect, the invention provides methods for distinguishing the occurrence of lacunar stroke or a predisposition for experiencing lacunar stroke from the occurrence of non-lacunar stroke or a predisposition for experiencing non-lacunar stroke. In some embodiments, the methods comprise:

a) determining a level of expression of a plurality of lacunar stroke-associated biomarkers in a biological sample from a patient, wherein the biomarkers are selected from Table 3; and b) comparing the level of expression of the lacunar stroke-associated biomarkers to the expression level of a plurality of stably expressed endogenous reference biomarkers;

wherein an increase of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3, CCDC114, AKAP9, BNC2, BZRAP1, CCL4, CHST2, CSF1, ERBB2, GBR56, GRAMD3, GRHL2, GRK4, ITIH4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, and ZNF827, and/or a decrease of the expression level of one or more biomarkers selected from the group consisting of HLA-DQA1, FLJ13773, QKI, MPZL3, FAM70B, LOC254128, IL8, CHML, STX7, VAPA, UGCG, PDXDC1, LRRC8B, STK4, GTF2H2, AGFG1, BTG1, CFDP1, CNPY2, FAM105A, GATM, GTF2H2B, IGHG1, IL18RAP, N4BP2, PHACTR1, RTKN2, SLC16A1, SOCS1, SPAG17, ST6GALNAC1, STK17B, STT3B, STX16, TBC1D12, TRIM4, UACA, and WHAMML2 compared to the expression level of the plurality of endogenous reference biomarkers is correlative with or indicates that the patient suffers from or is at risk of experiencing lacunar stroke; and/or wherein a decrease of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3, CCDC114, AKAP9, BNC2, BZRAP1, CCL4, CHST2, CSF1, ERBB2, GBR56, GRAMD3, GRHL2, GRK4, ITIH4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, and ZNF827, and an increase of the expression level of one or more biomarkers selected from the group consisting of HLA-DQA1, FLJ13773, QKI, MPZL3, FAM70B, LOC254128, IL8, CHML, STX7, VAPA, UGCG, PDXDC1, LRRC8B, STK4, GTF2H2, AGFG1, BTG1, CFDP1, CNPY2, FAM105A, GATM, GTF2H2B, IGHG1, IL18RAP, N4BP2, PHACTR1, RTKN2, SLC16A1, SOCS1, SPAG17, ST6GALNAC1, STK17B, STT3B, STX16, TBC1D12, TRIM4, UACA, and WHAMML2 compared to the expression level of the plurality of endogenous reference biomarkers is correlative with or indicates that the patient suffers from or is at risk of experiencing non-lacunar stroke;

thereby distinguishing the occurrence of lacunar stroke or the predisposition for experiencing lacunar stroke from the occurrence of non-lacunar stroke or a predisposition for experiencing non-lacunar stroke.

In a related aspect, the invention provides methods for diagnosing lacunar stroke or a predisposition for developing lacunar stroke. In some embodiments, the methods comprise determining a level of expression of a plurality of lacunar stroke-associated biomarkers in a biological sample from a patient, wherein an increase or decrease of the level compared to a control level is correlative with or indicates that the patient suffers from or is at risk of developing lacunar stroke;

wherein an increase of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3, CCDC114, AKAP9, BNC2, BZRAP1, CCL4, CHST2, CSF1, ERBB2, GBR56, GRAMD3, GRHL2, GRK4, ITIH4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, and ZNF827, and/or a decrease of the expression level of one or more biomarkers selected from the group consisting of HLA-DQA1, FLJ13773, QKI, MPZL3, FAM70B, LOC254128, IL8, CHML, STX7, VAPA, UGCG, PDXDC1, LRRC8B, STK4, GTF2H2, AGFG1, BTG1, CFDP1, CNPY2, FAM105A, GATM, GTF2H2B, IGHG1, IL18RAP, N4BP2, PHACTR1, RTKN2, SLC16A1, SOCS1, SPAG17, ST6GALNAC1, STK17B, STT3B, STX16, TBC1D12, TRIM4, UACA, and WHAMML2 compared to the control level is correlative with or indicates that the patient suffers from or is at risk of experiencing lacunar stroke, thereby diagnosing the occurrence of lacunar stroke or the predisposition for experiencing lacunar stroke. In some embodiments, the control is the expression level of one or more stably expressed endogenous reference biomarkers.

With respect to the embodiments, in some embodiments, an increase of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3 and CCDC114, and/or a decrease of the expression level of one or more biomarkers selected from the group consisting of HLA-DQA1, FLJ13773, QKI, MPZL3, FAM70B, LOC254128, IL8, CHML, STX7, VAPA, UGCG, PDXDC1, LRRC8B, STK4, GTF2H2, compared to the expression level of the plurality of endogenous reference biomarkers is correlative with or indicates that the patient suffers from or is at risk of experiencing lacunar stroke. In some embodiments, a decrease of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3 and CCDC114, and an increase of the expression level of one or more biomarkers selected from the group consisting of HLA-DQA1, FLJ13773, QKI, MPZL3, FAM70B, LOC254128, IL8, CHML, STX7, VAPA, UGCG, PDXDC1, LRRC8B, STK4, GTF2H2, compared to the expression level of the plurality of endogenous reference biomarkers is correlative with or indicates that the patient suffers from or is at risk of experiencing non-lacunar stroke.

In some embodiments, an increase of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, and ALS2CR11, and/or a decrease of the expression level of one or more biomarkers selected from the group consisting of HLA-DQA1, FLJ13773, QKI, MPZL3, FAM70B, LOC254128, IL8, CHML, STX7, VAPA, UGCG, and PDXDC1, compared to the expression level of the plurality of endogenous reference biomarkers is correlative with or indicates that the patient suffers from or is at risk of experiencing lacunar stroke. In some embodiments, a decrease of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, and ALS2CR11, and an increase of the expression level of one or more biomarkers selected from the group consisting of HLA-DQA1, FLJ13773, QKI, MPZL3, FAM70B, LOC254128, IL8, CHML, STX7, VAPA, UGCG, and PDXDC1, compared to the expression level of the plurality of endogenous reference biomarkers is correlative with or indicates that the patient suffers from or is at risk of experiencing non-lacunar stroke.

In some embodiments, an increase of the expression level of one or more biomarkers selected from the group consisting of RASEF, CALM1, TTC12, CCL3, CCL3L1, CCL3L3, CCDC78, PRSS23, LAIR2, C18orf49, UTS2, and LGR6, and/or a decrease of the expression level of one or more biomarkers selected from the group consisting of HLA-DQA1, FLJ13773, QKI, MPZL3, FAM70B, LOC254128, IL8, CHML, and STX7, compared to the expression level of the plurality of endogenous reference biomarkers is correlative with or indicates that the patient suffers from or is at risk of experiencing lacunar stroke. In some embodiments, a decrease of the expression level of one or more biomarkers selected from the group consisting of RASEF, CALM1, TTC12, CCL3, CCL3L1, CCL3L3, CCDC78, PRSS23, LAIR2, C18orf49, UTS2, LGR6, and PROCR, and an increase of the expression level of one or more biomarkers selected from the group consisting of HLA-DQA1, FLJ13773, QKI, MPZL3, FAM70B, LOC254128, IL8, CHML, and STX7, compared to the expression level of the plurality of endogenous reference biomarkers is correlative with or indicates that the patient suffers from or is at risk of experiencing non-lacunar stroke.

In some embodiments, an increase of the expression level of one or more biomarkers selected from the group consisting of RASEF, CALM1, TTC12, CCL3, CCL3L1, CCL3L3, CCDC78, PRSS23, and LAIR2, and/or a decrease of the expression level of one or more biomarkers selected from the group consisting of HLA-DQA1, FLJ13773, and QKI, compared to the expression level of the plurality of endogenous reference biomarkers is correlative with or indicates that the patient suffers from or is at risk of experiencing lacunar stroke. In some embodiments, a decrease of the expression level of one or more biomarkers selected from the group consisting of RASEF, CALM1, TTC12, CCL3, CCL3L1, CCL3L3, CCDC78, PRSS23, and LAIR2, and an increase of the expression level of one or more biomarkers selected from the group consisting of HLA-DQA1, FLJ13773, and QKI, compared to the expression level of the plurality of endogenous reference biomarkers is correlative with or indicates that the patient suffers from or is at risk of experiencing non-lacunar stroke.

In various embodiments, the expression levels of the biomarkers are concurrently or sequentially determined.

In some embodiments, the methods further comprise the step of obtaining a biological sample from the patient. In some embodiments, the biological sample is blood, serum or plasma.

In some embodiments, the method is performed in a clinical laboratory. In some embodiments, the method is performed at the point of care.

In some embodiments, the plurality of stably expressed endogenous reference biomarkers are selected from USP7, MAPRE2, CSNK1G2, SAFB2, PRKAR2A, PI4KB, CRTC1, HADHA, MAP1LC3B, KAT5, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110 and PEX16. In some embodiments, the lacunar stroke-associated biomarkers are overexpressed or underexpressed at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, or more, in comparison to the expression levels of a plurality of stably expressed endogenous reference biomarkers. In some embodiments, the expression levels of 2, 3, 4, 5, 6, 7, 8, 9, 10, 15, 20, 25, 30, 35, or all, the endogenous reference biomarkers selected from the group consisting of USP7, MAPRE2, CSNK1G2, SAFB2, PRKAR2A, PI4KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

In some embodiments, the level of expression of about 15-85, 20-70, 30-60 or 40-50 lacunar stroke-associated biomarkers are determined. In some embodiments, about 15, 20, 25, 30, 35, 40, 45, 50, 55, 60, 65, 70, 75, 80, 85, 90, 95 or 100 lacunar stroke-associated biomarkers are determined. In some embodiments, the expression levels of at least about 3, 5, 10, 15, 20, 25, 30 or more lacunar stroke-associated biomarkers from Table 3 are determined. In some embodiments, the expression levels of at least about 3, 5, 10, 15, 20, 25, 30 or more lacunar stroke-associated biomarkers from Table 4 are determined.

In some embodiments, the determining step is performed within 72 hours, for example, within 60 hours, 48 hours, 36 hours, 24 hours, 12 hours, 6 hours or 3 hours, after a suspected ischemic event.

In some embodiments, the patient is asymptomatic. In some embodiments, the patient is exhibiting symptoms of ischemic stroke, e.g., of having experienced an ischemic event, of experiencing an ischemic event, or of an imminent ischemic event. In some embodiments, the patient has suffered an ischemic event. In some embodiments, the determining step is performed at 3 or fewer hours after the ischemic event. In some embodiments, the determining step is performed 3 or more hours after the ischemic event.

In some embodiments, the patient has at least one vascular risk factor. In some embodiments, the patient has experienced a small deep infarction (SDI). In some embodiments, the patient shows evidence of microhemorrhage. In some embodiments, the patient is non-Caucasian. In some embodiments, the patient does not have arterial disease ipsilateral to the stroke.

In various embodiments, the methods, particularly performance of the comparison step, are computer implemented. Such computer-implemented methods may also provide an output of the comparison of expression levels.

Methods for determining the occurrence or predisposition of a lacunar stroke may further comprise the step of determining whether the patient has suffered a myocardial infarction or whether the patient has vascular risk factors. Methods for determining the occurrence or predisposition of a lacunar stroke may further comprise the step of determining whether the patient has evidence of microhemorrhage or whether the patient has arterial disease or whether the patient has cerebral vascular disease. Methods for determining the occurrence or predisposition of a lacunar stroke may further comprise the step of determining whether the patient has suffered a small deep infarction (SDI).

In some embodiments, the level of expression of the biomarker is determined at the transcriptional level. In some embodiments, the level of expression is determined by detecting hybridization of a lacunar stroke-associated gene probe to gene transcripts of the biomarkers in the biological sample.

In some embodiments, the methods further comprise the step of performing additional diagnostic tests useful for identifying whether a patient has experienced or has a predisposition to experience lacunar stroke, e.g., based on imaging or ultrasound techniques. In various embodiments, the methods further comprise performing one or more diagnostic tests selected from the group consisting of X-ray computed tomography (CT), magnetic resonance imaging (MRI) brain scanning, vascular imaging of the head and neck with doppler or magnetic resonance angiography (MRA), CT angiography (CTA), electrocardiogram (e.g., EKG or ECG), cardiac ultrasound and cardiac monitoring. In various embodiments, the patient is subjected to cardiac monitoring for at least 2 days, e.g., for 2-30 days or for 7-21 days, e.g., for 2, 5, 7, 10, 12, 14, 18, 20, 21, 25, 28, 30, or more days, as appropriate. In various embodiments, the location of the infarction is determined. An infarction located in a subcortical region of the brain is associated with or correlated with a diagnosis of lacunar stroke. An infarction located in a cortical region of the brain, e.g., in regions of the penetrating arteries, e.g., basal ganglia, thalamus, internal capsule, corona radiata and/or pons, is associated with or correlated with a diagnosis of non-lacunar stroke. In some embodiments, the size of the infarction is determined.

In some embodiments, the methods further comprise the step of recommending or providing a regime of treatment to the patient appropriate to the determined cause of stroke. For example, in patients diagnosed as experiencing or having a predisposition for experiencing lacunar stroke, the methods further provide for recommending or providing a regime of treatment or prevention for lacunar stroke.

In various embodiments, the methods may further comprise the step of determining the cause or risk of ischemic stroke if the patient has experienced or has a predisposition to experience non-lacunar stroke. The methods may further comprise the step of recommending or providing a regime of treatment to the patient appropriate to the determined cause of non-lacunar stroke. For example, in patients diagnosed as experiencing or having a predisposition for experiencing cardioembolic stroke, the methods further provide for recommending or providing a regime of treatment or prevention for cardioembolic stroke. In patients diagnosed as experiencing or having a predisposition for experiencing carotid stenosis, the methods further provide for recommending or providing a regime of treatment or prevention for carotid stenosis. In patients diagnosed as experiencing or having a predisposition for experiencing atrial fibrillation, the methods further provide for recommending or providing a regime of treatment or prevention for atrial fibrillation. In patients diagnosed as experiencing or having a predisposition for experiencing transient ischemic attack, the methods further provide for recommending or providing a regime of treatment or prevention for transient ischemic attack.

With respect to embodiments for determination of the level of expression of the biomarkers, in some embodiments, the level of expression of the biomarker is determined at the transcriptional level. For example, in some embodiments, the level of expression is determined by detecting hybridization of an ischemic stroke-associated gene probe to gene transcripts of the biomarkers in the biological sample. In some embodiments, the hybridization step is performed on a nucleic acid array chip. In some embodiments, the hybridization step is performed in a microfluidics assay plate. In some embodiments, the level of expression is determined by amplification of gene transcripts of the biomarkers. In some embodiments, the amplification reaction is a polymerase chain reaction (PCR).

In some embodiments, the level of expression of the biomarker is determined at the protein level.

In a further aspect, the invention provides a solid support comprising a plurality of nucleic acids that hybridize to a plurality of lacunar stroke-associated genes selected from the group consisting of HLA-DQA1, FLJ13773, RASEF, CALM1, QKI, TTC12, CCL3///CCL3L1///CCL3L3, CCDC78, PRSS23, LAIR2, C18orf49, MPZL3, UTS2, FAM70B, UTS2, LOC254128, LGR6, IL8, CHML, STX7, PROCR, VAPA, LAG3, OASL, LOC100132181, HLA-DRB4, CCL2, UGCG, PDXDC1, ALS2CR11, SCAND2, GBP4, RUNX3, LRRC8B, TSEN54, UBA7, STK4, FAM179A, TGFBR3, CCDC114, GTF2H2, AKAP9, BNC2, BZRAP1, CCL4, CHST2, CSF1, ERBB2, GBR56, GRAMD3, GRHL2, GRK4, ITIH4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, ZNF827, AGFG1, BTG1, CFDP1, CNPY2, FAM105A, GATM, GTF2H2, IGHG1, IL18RAP, N4BP2, PHACTR1, QKI, RTKN2, SLC16A1, SOCS1, SPAG17, ST6GALNAC1, STK17B, STT3B, STX16, TBC1D12, TRIM4, UACA, and WHAMML2. As appropriate, the solid support may comprise, 2, 5, 10, 15, 20, 25, 30, 35, 40, 45, 50, 55, 60, 65, 70, 75, 80, 85, 90, 95 or more, nucleic acids that hybridize to a plurality of lacunar stroke-associated genes. The solid support may be provided in a kit.

In some embodiments, the solid support comprises a plurality of nucleic acids that hybridize to a plurality of lacunar stroke-associated genes selected from the group consisting of HLA-DQA1, FLJ13773, RASEF, CALM1, QKI, TTC12, CCL3///CCL3L1///CCL3L3, CCDC78, PRSS23, LAIR2, C18orf49, MPZL3, UTS2, FAM70B, UTS2, LOC254128, LGR6, IL8, CHML, STX7, PROCR, VAPA, LAG3, OASL, LOC100132181, HLA-DRB4, CCL2, UGCG, PDXDC1, ALS2CR11, SCAND2, GBP4, RUNX3, LRRC8B, TSEN54, UBA7, STK4, FAM179A, TGFBR3, CCDC114 and GTF2H2.

In some embodiments, the solid support comprises a plurality of nucleic acids that hybridize to a plurality of lacunar stroke-associated genes selected from the group consisting of HLA-DQA1, FLJ13773, RASEF, CALM1, QKI, TTC12, CCL3///CCL3L1///CCL3L3, CCDC78, PRSS23, LAIR2, C18orf49, MPZL3, UTS2, FAM70B, UTS2, LOC254128, LGR6, IL8, CHML, STX7, PROCR, VAPA, LAG3, OASL, LOC100132181, HLA-DRB4, CCL2, UGCG, PDXDC1, and ALS2CR11.

In some embodiments, the solid support comprises a plurality of nucleic acids that hybridize to a plurality of lacunar stroke-associated genes selected from the group consisting of HLA-DQA1, FLJ13773, RASEF, CALM1, QKI, TTC12, CCL3///CCL3L1///CCL3L3, CCDC78, PRSS23, LAIR2, C18orf49, MPZL3, UTS2, FAM70B, UTS2, LOC254128, LGR6, IL8, CHML, and STX7.

In some embodiments, the solid support comprises a plurality of nucleic acids that hybridize to a plurality of lacunar stroke-associated genes selected from the group consisting of HLA-DQA1, FLJ13773, RASEF, CALM1, QKI, TTC12, CCL3///CCL3L1///CCL3L3, CCDC78, PRSS23, and LAIR2.

In various embodiments, the solid support further comprises a plurality of nucleic acids that hybridize to a plurality of endogenous reference genes selected from the group consisting of USP7, MAPRE2, CSNK1G2, SAFB2, PRKAR2A, PI4KB, CRTC1, HADHA, MAP1LC3B, KAT5, CDC2L1///CDC2L2, GTSE1, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16.

In various embodiments, the solid support further comprises a plurality of nucleic acids that hybridize to a plurality of ischemic stroke-associated biomarkers selected from the group consisting of FAT3, GADL1, CXADR, RNF141, CLEC4E, TIMP2, ANKRD28, TIMM8A, PTPRD, CCRL1, FCRL4, DLX6, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, MCTP1, SH3GL3, PGM5, CCDC144C///LOC100134159, LECT2, SHOX, TBX5, SPTLC3, SNIP, RBMS3, P704P, THSD4, SNRPN, GLYATL1, DKRZP434L187, OVOL2, SPIB, BXDC5, UNC5B, ASTN2, FLJ35934, CCDC144A, ALDOAP2, LDB3, LOC729222///PPFIBP1, HNRNPUL2, ELAVL2, PRTG, FOXA2, SCD5, LOC283027, LOC344595, RPL22, LOC100129488 and RPL22.

In various embodiments, the solid support further comprises a plurality of nucleic acids that hybridize to a plurality of cardioembolic stroke-associated biomarkers selected from the group consisting of IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP, LRRC37A3, LOC284751, CD46, ENPP2, C19orf28, TSKS, CHURC1, ADAMTSL4, FLJ40125, CLEC18A, ARHGEF12, C16orf68, TFDP1 and GSTK1.

In various embodiments, the solid support further comprises a plurality of nucleic acids that hybridize to a plurality of carotid stenosis-associated biomarkers selected from the group consisting of NT5E, CLASP2, GRM5, PROCR, ARHGEF5, AKR1C3, COL13A1, LHFP, RNF7, CYTH3, EBF1, RANBP10, PRSS35, C12orf42, LOC100127980, FLJ31945, LOC284751, LOC100271832, MTBP, ICAM4, SHOX2, DOPEY2, CMBL, LOC146880, SLC20A1, SLC6A19, ARHGEF12, C16orf68, GIPC2 and LOC100144603.

In various embodiments, the solid support further comprises a plurality of nucleic acids that hybridize to a plurality of atrial fibrillation-associated biomarkers selected from the group consisting of SMC1A, SNORA68, GRLF1, SDC4, HIPK2, LOC100129034, CMTM1, TTC7A, LRRC43, MIF///SLC2A11, PER3, PPIE, COL13A1, DUSP16, LOC100129034, BRUNOL6, GPR176, C6orf164 and MAP3K7IP1.

In various embodiments, the solid support further comprises a plurality of nucleic acids that hybridize to a plurality of transient ischemic attack-associated biomarkers selected from the group consisting of GABRB2, ELAVL3, COL1A1, SHOX2, GABRB2, TWIST1, DPPA4, DKFZP434P211, WIT1, SOX9, DLX6, ANXA3, EPHA3, SOX11, SLC26A8, CCRL1, FREM2, STOX2, ZNF479, LOC338862, ASTN2, FOLH1, SNX31, KREMEN1, ZNF479, ALS2CR11, FIGN, RORB, LOC732096, GYPA, ALPL, LHX2, GALNT5, SRD5A2L2, GALNT14, OVOL2, BMPR1B, UNC5B, ODZ2, ALPL, RASAL2, SHOX, C19orf59, ZNF114, SRGAP1, ELAVL2, NCRNA00032, LOC440345, FLJ30375, TFPI, PTGR1, ROBO1, NR2F2, GRM5, LUM, FLJ39051, COL1A2, CASP5, OPCML, TTC6, TFAP2B, CRISP2, SOX11, ANKRD30B, FLJ39051, SCN2A, MYNN, FOXA2, DKFZP434B061, LOC645323, SNIP, LOC645323, LOC374491, ADAM30, SIX3, FLJ36144, CARD8, KREMEN1, RP1-127L4.6, FAM149A, B3GAT2, SPOCK3, G30, ITGBL1, IQGAP3, C7orf45, ZNF608, LOC375010, LRP2, TGFB2, SHOX2, HOXC4///HOXC6, ELTD1, FAM182B///RP13-401N8.2, PRO0478, LIFR, FOLH1, EHF, NDST3, BRUNOL5, LOC728460, PDE1A, POU2AF1, FAT1, PCDH11X///PCDH11Y, FLJ37786, SLC22A4, DHRS13, EHF, MEG3, PIWIL1, LOC203274, LOC100133920///LOC286297, DMRT1, ADM, VWA3B, GAFA3, HESX1, ADAMDEC1, CAV1, LAMB4, TPTE, PPP1R1C, HPSE, AIM2, RUNDC3B, CARD16, FAM124A, MGC39584, OSM, RFX2, MYBPC1, LTBR, C18orf2, SNRPN, FLJ36031, IL1B, TRPM1, OSTCL, MAPK14, KCNJ15///LOC100131955, FIGN, HNT, S100A12, CHIT1, C7orf53, FAM13A1, GNAO1, MAPK14, FAM55D, PRKD2, LIMK2, C18orf54, IGFBP5, EVI1, PLSCR1, FOXC1, LOC646627, ZNF462, CNTLN, ZNF438, DEFB105A///DEFB105B, LOC340017, C1orf67, ACSL1, ADH1B, SLC2A14///SLC2A3, IL1B, ST3GAL4, UBE2J1, PNPLA3, PAPPA, NBPF10///RP11-94I2.2, SFXN1, SPIN3, UNC84A, OLFM2, PPM1K, P2RY10, ZNF512B, MORF4L2, GIGYF2, ERAP2, SLFN13, LOC401431, MED6, BAIAP2L1///LOC100128461, LNPEP, MBNL1, NOS3, MCF2L, KIAA1659, SCAMP5, LOC648921, ANAPC5, SPON1, FUS, GPR22, GAL3ST4, METTL3, LOC100131096, FAAH2, SMURF2, SNRPN, FBLN7, GLS, G3BP1, RCAN3, EPHX2, DIP2C, CCDC141, CLTC, FOSB, CACNA1I, UNQ6228, ATG9B, AK5, SPIN3, RBM14, SNRPN, MAN1C1, HELLS, EDAR, SLC3A1, ZNF519, LOC100130070///LOC100130775///LOC100131787///LOC100131905///LOC100132291///LOC100132488///RPS27, ZC3H12B, IQGAP2, SOX8, WHDC1L2, TNPO1, TNFRSF21, TSHZ2, DMRTC1///DMRTC1B, GSTM1, GSTM2, PNMA6A, CAND1, CCND3, GSTM1, and GUSBL2.

In some embodiments, the solid support is a microarray. In various embodiments, the microarray has 1000 or fewer hybridizing nucleic acids, for example, 900, 800, 700, 600, 500 or fewer hybridizing nucleic acids. In various embodiments, the microarray does not comprise nucleic acids that hybridize to genes whose expression is not correlative of or associated with ischemia.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, et al., CURRENT PROTOCOLS IN MOLECULAR BIOLOGY, 1990-2008, Wiley Interscience), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

The term "small deep infarct" or "small deep infarction" or "SDI" interchangeably refer to focal infarction of the brain due to an uncertain cause, including but not limited to, cardioembolic, atheroembolic, atherosclerotic disease of the parent artery or disease of the perforating artery.

The term "lacunar stroke" or "lacune" interchangeably refer to focal infarction of the brain due to perforating branch occlusion from microatheroma or lipohyalinosis. Implicit in this definition of lacunar stroke is that the: 1) infarction is not due to cardioembolic source; 2) infarction is not due to atherosclerotic disease of parent arteries; 3) infarction occurs in regions of the brain supplied by penetrating arteries, e.g., basal ganglia, thalamus, internal capsule, corona radiata or pons; 4) lacunar stroke is oftentimes associated with the presence of hypertension, diabetes or other vascular risk factors; and 5) infarcts tend to be smaller, generally less than 50 mm in diameter. When the cause of stroke is uncertain or likely other than perforating artery disease, then the more general term—small deep infarct—is appropriate. See, e.g., Caplan, Stroke (2003) 34(3):653-9; Norrving, Pract Neurol (2008) 8:222-228; Lastilla, Clin Exp Hypertens. (2006) 28(3-4):205-15; and Arboix and Marti-Vilalta, Expert Rev Neurother. (2009) 9(2):179-96.

The term "transient ischemic attack," "TIA," or "mini-stroke" interchangeably refer to a change in the blood supply to a particular area of the brain, resulting in brief neurologic dysfunction that persists, by definition, for less than 24 hours. By definition, a TIA resolves within 24 hours, but most TIA symptoms resolve within 1 hour. If symptoms persist longer, then it is categorized as a stroke. Symptoms include temporary loss of vision (typically amaurosis fugax); difficulty speaking (aphasia); weakness on one side of the body (hemiparesis); numbness or tingling (paresthesia), usually on one side of the body, and dizziness, lack of coordination or poor balance. The symptoms of a TIA usually last a few minutes and with resolution of most symptoms within 60 minutes.

"Reference expression profile" refers to the pattern of expression of a set of genes (e.g., a plurality of the genes set forth in Tables 3 and 4) differentially expressed (i.e., overexpressed or underexpressed) in ischemia relative to a control (e.g., the expression level in an individual free of an ischemic event or the expression level of a stably expressed endogenous reference biomarker). A gene from Tables 3 and 4 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4- or 3.5-fold higher than the level in a control is a gene overexpressed in ischemia and a gene from Tables 3 and 4 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4- or 3.5-fold lower than the level in a control is a gene underexpressed in ischemia. Alternately, genes that are expressed at a level that is at least about 10%, 20%, 30%, 40%, 50%, 60%, 70%, 80%, 90%, or 100% higher than the level in a control is a gene overexpressed in ischemia and a gene that is expressed at a level that is at least about 10%, 20%, 30%, 40%, 50%, 60%, 70%, 80%, 90%, or 100% lower than the level in a control is a gene underexpressed in ischemia.

A "plurality" refers to two or more, for example, 2, 3, 4, 5, 6, 7, 8, 9, 10, 11, 12, 13, 14, 15, 16, 17, 18, 19, 20, 21, 22, 23 or more (e.g., genes). In some embodiments, a plurality refers to concurrent or sequential determination of about 15-85, 20-60 or 40-50 genes, for example, about 15, 20, 25, 30, 35, 40, 45, 50, 55, 60, 65, 70, 75, 80, 85, 90, 95 or 100, or more, genes. In some embodiments, "plurality" refers to all genes listed in one or more tables, e.g., all genes listed in Tables 3 and 4.

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800,992. Arrays may be packaged in such a manner as to allow for diagnostics or other manipulation of an all-inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent hybridization conditions are selected to be about 5-10° C. lower than the thermal melting point for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of an ischemia-associated gene (e.g., a gene set forth in Tables 3 and 4), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length, or over the full length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to ischemia-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (on the internet at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

By "host cell" is meant a cell that contains an expression vector and supports the replication or expression of the expression vector. Host cells may be, for example, prokaryotic cells such as *E. coli* or eukaryotic cells such as yeast cells or mammalian cells such as CHO cells.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

BRIEF DESCRIPTION OF THE DRAWINGS

FIGS. 4A and 4B illustrate a probability plot of the predicted diagnosis of lacunar and non-lacunar stroke based on 10-fold cross-validation analysis using the linear discriminant analysis model for the 41 probesets (40 genes). 4A illustrates the predicted probability of lacunar and non-lacunar stroke in the 30 patients diagnosed clinically as lacunar stroke. Eight subjects were predicted to have a gene expression profile similar to those of non-lacunar stroke, and 22 were predicted to be lacunar stroke. 4B illustrates the predicted probability of non-lacunar and lacunar stroke in the 86 patients with non-lacunar stroke. Eighty of the 86 were correctly predicted to be non-lacunar stroke.

DETAILED DESCRIPTION

1. Introduction

Figure 1:
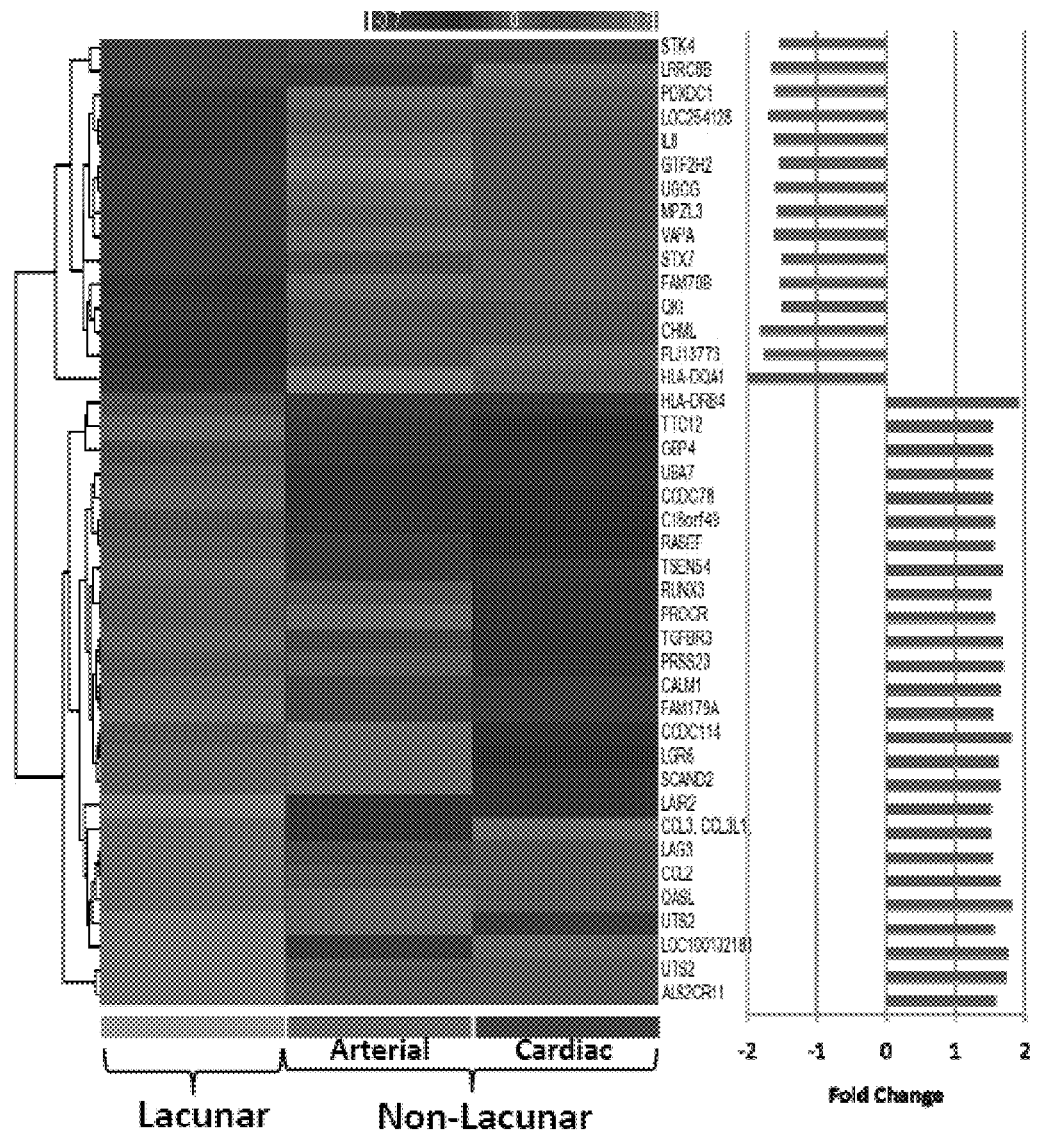
FIGS. 1A and 1B illustrate how gene expression analysis can be used to distinguish lacunar from non-lacunar stroke. 1A provides an illustrative cluster plot of 41 probesets corresponding to 40 genes that discriminate lacunar from non-lacunar stroke. Genes are shown on the y-axis and strokes of lacunar, and non-lacunar (arterial and cardioembolic) etiologies are shown on the x-axis. Up regulated genes are shown in red, and down regulated genes in blue. 1B illustrates the fold change of the 41 probesets. There is a group of genes that are down-regulated in lacunar stroke and up regulated in non-lacunar stroke. Similarly, there is a group of genes that are up-regulated in lacunar stroke and down regulated in non-lacunar stroke. These genes can be used to discriminate lacunar from non-lacunar stroke.

Small deep infarcts including lacunar stroke account for greater than one quarter of all ischemic strokes and are associated with increased risk of cardiovascular disease and dementia. Though lipohyalinosis of small penetrating arteries (lacunar stroke) is the most common cause, emboli of arterial or cardiac origin are also causes. Determining which small deep infarcts are caused by lacunar disease, arterial emboli, or cardiac emboli is challenging, but nevertheless important to deliver optimal stroke prevention therapy.

184 ischemic strokes were analyzed to determine gene expression profiles useful to distinguish lacunar from non-lacunar causes of small deep infarcts. Lacunar stroke was defined as a lacunar syndrome associated with infarction <15 mm of the striatum, internal capsule, corona radiata, thalamus or pons. RNA was isolated from whole blood and processed on whole genome microarrays. Differentially expressed genes between acute lacunar strokes (n=30) and non-lacunar strokes (n=86) were identified (false discovery rate ≤0.05, fold change>|1.5|). A prediction model able to discriminate lacunar from non-lacunar stroke was generated using linear discriminant analysis and evaluated using cross-validation and a second test cohort of non-lacunar strokes (n=36). The model was then applied to predict etiology in small deep infarcts of unclear cause (size >15 mm or small deep infarct with potential embolic source) (n=32). A 41 gene profile discriminated lacunar from non-lacunar strokes with greater than 90% sensitivity and specificity. Of the 32 small deep infarcts of unclear cause, 17 were predicted to be of lacunar etiology and 15 were predicted to be of non-lacunar etiology. Independent predictors of lacunar stroke were non-Caucasian race/ethnicity and absence of ipsilateral arterial disease. The identified profile largely represents differences in immune response between stroke subtypes important to lacunar stroke. Accordingly, the present invention is based, in part, on the discovery that gene expression profiles can distinguish lacunar from non-lacunar strokes. Small deep infarcts of unclear cause were frequently predicted to be of non-lacunar etiology; subsequent work-up and analysis can be performed to identify potential cardio-embolic and/or arterial causes. Gene expression profiling may also be used to determine the clinical and treatment implications of small deep infarcts predicted to be of non-lacunar etiology.

Accordingly, the present invention is based, in part, on the discovery that RNA expression profiling can be used to differentiate stroke of lacunar etiology from non-lacunar stroke. The invention provides a list of 41 probesets (corresponding to 40 genes) that have greater than 90% sensitivity and specificity to distinguish lacunar stroke from non-lacunar strokes. The genes identified herein to be associated with the occurrence of and/or risk of experiencing lacunar stroke find use to diagnose lacunar stroke based upon an RNA expression profile. The use of the presently identified gene allow for the use of a blood test for the rapid diagnosis of a lacunar cause of stroke.

In practice, the level of expression of genes associated with the occurrence or risk of lacunar stroke can be measured in the blood of patients with an ischemic stroke. The expression of these genes can be assessed using any applicable method in the art, including, e.g., RT-PCR, microarrays or other technology. In various embodiments, the expression of these target genes can be normalized to internal control genes, which are known in the art. A panel of control genes that are specific for ischemic stroke have been developed and are quite reliable. The endogenous control genes have fairly constant expression over many age groups, different diseases, and both genders. Once the RNA expression levels of the target genes (i.e., lacunar stroke-associated genes) are measured, and the RNA levels of the control genes are measured, then the target gene expression is normalized to the control genes. The expression levels of the normalized target genes can then be applied to a linear discriminant analysis model to predict whether the blood sample is from a patient who has experience or is at risk of experiencing lacunar stroke and the probability that this is the case. Determining the expression levels of the presently identified lacunar stroke-associated genes, the sensitivity and specificity for prediction is greater than 90% for lacunar versus non-lacunar stroke.

A blood test for the diagnosis of stroke is useful in several situations. For example, the gene expression panel can be used to predict whether lacunar stroke is the cause of stroke in patients with small deep infarcts of the brain. About 25% of all stroke patients have small deep infarcts. These small deep infarcts can be caused by lacunar small vessel disease, but also by atherosclerotic disease or larger parent arteries and embolism form a cardiac source. An embolic atherosclerotic cause of stroke warrants a different investigative strategy and treatment than a lacunar small vessel cause of stroke. In particular, it is important to diagnose disease that would guide appropriate disease treatment and management including the two most effective treatments for stroke: carotid surgery for symptomatic carotid stenosis and warfarin for symptomatic atrial fibrillation. Thus, ascertaining the etiology of small deep infarcts is of clinical importance.

Currently, patients presenting with a small deep infarct are mostly labeled lacunar, and treated with anti-platelet agents. A diagnosis based on the expression levels of the presently identified lacunar stroke-associated genes would identify the lacunar and non-lacunar strokes, and thus guide appropriate treatment for stroke patients. The presently identified lacunar stroke-associated genes further find use for diagnosing patients who have experienced or are at risk of experiencing Transient Ischemic Attacks. In these patients, the cause is often unknown. Thus, a blood test predicting the cause of the TIA could help prevent or ameliorate strokes in these patients.

The diagnosis of lacunar stroke presently requires a neurologist to take a history, perform an examination and then confirm using X-ray computed tomography (CT) or magnetic resonance imaging (MRI) brain scanning, in addition to vascular imaging of the head and neck with doppler or magnetic resonance angiography (MRA) or CT angiography (CTA); an electrocardiogram (EKG or ECG), cardiac ultrasound and cardiac monitoring; and a series of blood tests. Even with all these investigations, some uncertainty in the diagnosis of lacunar stroke remains, as potential arterial and cardiac causes can be missed. The present panel of lacunar stroke-associated genes provides a rapid blood-based test that can be performed at the point of care or in a clinical laboratory at low cost. Diagnosis of the presence or absence of occurrence or risk of lacunar stroke using the presently identified panel of lacunar stroke-associated genes adds confidence to a physicians' diagnosis of lacunar or non-lacunar stroke.

2. Patients Who can Benefit from the Present Methods

Individuals who will benefit from the present methods may be exhibiting symptoms of ischemic stroke, and in particular, a small deep infarct (SDI). In some embodiments, the subject has experienced an ischemic event. For example, the subject may have suffered or be currently experiencing a small deep infarct, a transient ischemic attack (TIA), an ischemic stroke, a myocardial infarction, peripheral vascular disease, or venous thromboembolism. The subject may have or have been diagnosed with cerebral vascular disease.

Alternatively, the subject may be suspected of having experienced an ischemic event, and in particular, a small deep infarct (SDI). Brain imaging on the patient may indicate microhemorrhage and/or blood-brain permeability. In some embodiments, the levels of expression of the panel of biomarkers is determined within 3 hours of a suspected ischemic event. In some embodiments, the levels of expression of the panel of biomarkers is determined at 3 or more hours after a suspected ischemic event. In some embodiments, the levels of expression of the panel of biomarkers is determined within 6, 12, 18, 24, 36, 48 or 72 hours of a suspected ischemic event.

In some cases, the subject is asymptomatic, but may have a risk or predisposition to experiencing ischemic stroke, e.g., based on genetics, familial history, a related disease condition, environment or lifestyle. In some embodiments, the patient has one or more vascular risk factors, e.g., hypertension, diabetes mellitus, hyperlipidemia, or tobacco smoking. In some embodiments, the subject is non-Caucasian, for example, Asian, African-American or Latino or of Asian, African-American or Latino descent.

Patients presenting with clinical symptoms of lacunar infarcts or diagnosed as having lacunar syndrome will also benefit from the present diagnostic gene expression profiling. Clinical symptoms of lacunar infarcts include pure motor hemiparesis
pure sensory stroke
sensorimotor stroke
dysarthria-clumsy hand syndrome
ataxic hemiparesis Face, arm and leg involvement are characteristic of the first three listed symptoms. A component of ataxia is also present in the last two. Patients with a lacunar syndrome typically have no aphasia, no visuospatial disturbance, no visual field defect, generally no clear disturbance of brainstem function such as pupil abnormatities and eye movement disturbances, and no decreased level of consciousness (as a direct effect rather than as a complication of the stroke) at any time after the stroke. See, Norrving, *Pract Neurol* (2008) 8:222-228.

3. Biomarkers Useful for the Prediction or Diagnosis of Lacunar Stroke, or for Distinguishing Lacunar Stroke from Non-Lacunar Stroke Biomarkers useful for the prediction, diagnosis or confirmation of the occurrence of lacunar stroke, or for distinguishing lacunar stroke from non-lacunar stroke (e.g., non-lacunar small deep infarct (SDI)) are listed in Tables 3 and 4. Determination of the expression levels of a plurality of the biomarkers of Tables 3 and/or 4 can be performed for the prediction, diagnosis or confirmation of the occurrence of lacunar stroke in conjunction with other biomarkers known in the art for the prediction, diagnosis or confirmation of the occurrence of ischemic stroke, SDI and/or lacunar stroke, in conjunction with other methods known in the art for the diagnosis of ischemic stroke, SDI and/or lacunar stroke, in conjunction with biomarkers described herein and known in the art useful for determining the cause of ischemic stroke and/or in conjunction with methods known in the art for determining the cause of ischemic stroke.

Determination of the expression levels of a plurality of the biomarkers of Tables 3 and/or 4 can be performed for the prediction, diagnosis or confirmation of the occurrence of stroke can also be performed independently, e.g., to diagnose that a lacunar stroke has occurred, to distinguish lacunar stroke from non-lacunar stroke or non-lacunar SDI, or to determine the risk that a patient may suffer a lacunar stroke.

As appropriate, the expression levels of at least about 3, 5, 10, 15, 20, 25, 30, 40, 50, 60, 70, 80 or more biomarkers from Table 3 or Table 4 are determined. In some embodiments, the expression levels of a plurality of biomarkers in Table 3 or Table 4 are determined. In some embodiments, the expression levels of all listed biomarkers in Table 3 or Table 4 are determined.

In some embodiments, the level of expression of biomarkers indicative of the occurrence of lacunar stroke is determined within 72 hours, for example, within 60, 48, 36, 24, 12, 6 or 3 hours of a suspected ischemic event. An increased expression level of one or more lacunar stroke-associated biomarkers of Table 3 selected from the group consisting of AKAP9, ALS2CR11, BNC2, BZRAP1, C18orf49, CALM1, CCDC114, CCDC78, CCL2, CCL3, CCL3L1, CCL3L3, CCL4, CHST2, CSF1, ERBB2, FAM179A, GBP4, GBR56, GRAMD3, GRHL2, GRK4, HLA-DRB4, ITIH4, KIAA1618, LAG3, LAIR2, LGR6, LOC100132181, LOC147646, LOC150622, LOC161527, OASL, PLEKHF1, PRKD2, PROCR, PRSS23, RASEF, RGNEF, RUNX3, SCAND2, SESN2, SLAMF7, SPON2, STAT1, SYNGR1, TRX21, TGFBR3, TMEM67, TSEN54, TTC12, TUBE1, UBA7, UTS2, and ZNF827, is correlative with or indicates that the patient suffers from or is at risk of developing lacunar stroke. A decreased expression level of one or more lacunar stroke-associated biomarkers of Table 3 selected from the group consisting of AGFG1, BTG1, CFDP1, CHML, CNPY2, FAM105A, FAM70B, F1113773, GATM, GTF2H2, GTF2H2B, HLA DQA1, IGHG1, IL18RAP, IL8, LOC254128, LRRC8B, MPZL3, N4BP2, PDXDC1, PHACTR1, QKI, RTKN2, SLC16A1, SOCS1, SPAG17, ST6GALNAC1, STK17B, STK4, STT3B, STX16, STX7, TBC1D12, TRIM4, UACA, UGCG, VAPA, and WHAMML2 is correlative with or indicates that the patient suffers from or is at risk of developing lacunar stroke.

Conversely, a decreased expression level of one or more lacunar stroke-associated biomarkers of Table 3 selected from the group consisting of AKAP9, ALS2CR11, BNC2, BZRAP1, C18orf49, CALM1, CCDC114, CCDC78, CCL2, CCL3, CCL3L1, CCL3L3, CCL4, CHST2, CSF1, ERBB2, FAM179A, GBP4, GBR56, GRAMD3, GRHL2, GRK4, HLA-DRB4, ITIH4, KIAA1618, LAG3, LAIR2, LGR6, LOC100132181, LOC147646, LOC150622, LOC161527, OASL, PLEKHF1, PRKD2, PROCR, PRSS23, RASEF, RGNEF, RUNX3, SCAND2, SESN2, SLAMF7, SPON2, STAT1, SYNGR1, TRX21, TGFBR3, TMEM67, TSEN54, TTC12, TUBE1, UBA7, UTS2, and ZNF827, is correlative with or indicates that the patient suffers from or is at risk of developing non-lacunar stroke. Similarly, an increased expression level of one or more lacunar stroke-associated biomarkers of Table 3 selected from the group consisting of AGFG1, BTG1, CFDP1, CHML, CNPY2, FAM105A, FAM70B, FLJ13773, GATM, GTF2H2, GTF2H2B, HLA DQA1, IGHG1, IL18RAP, IL8, LOC254128, LRRC8B, MPZL3, N4BP2, PDXDC1, PHACTR1, QKI, RTKN2, SLC16A1, SOCS1, SPAG17, ST6GALNAC1, STK17B, STK4, STT3B, STX16, STX7, TBC1D12, TRIM4, UACA, UGCG, VAPA, and WHAMML2 is correlative with or indicates that the patient suffers from or is at risk of developing non-lacunar stroke.

In some embodiments, the level of expression of biomarkers indicative of the occurrence of lacunar stroke is determined within 72 hours, for example, within 60, 48, 36, 24, 12, 6 or 3 hours of a suspected ischemic event. An increased expression level of one or more lacunar stroke-associated biomarkers of Table 4 selected from the group consisting of HLA-DRB4, TTC12, GBP4, UBA7, CCDC78, C18orf49, RASEF, TSEN54, RUNX3, PROCR, TGFBR3, PRSS23, CALM1, FAM179A, CCDC114, LGR6, SCAND2, LAIR2, CCL3, CCL3L1, CCL3L3, LAG3, CCL2, OASL, UTS2, LOC100132181 and ALS2CR11, is correlative with or indicates that the patient suffers from or is at risk of developing lacunar stroke. A decreased expression level of one or more lacunar stroke-associated biomarkers of Table 4 selected from the group consisting of STK4, LRRC8B, PDXDC1, LOC254128, IL8, GTF2H2, UGCG, MPZL3, VAPA, STX7, FAM70B, QKI, CHML, FLJ13773, HLA-DQA1 is correlative with or indicates that the patient suffers from or is at risk of developing lacunar stroke.

Conversely, a decreased expression level of one or more lacunar stroke-associated biomarkers of Table 4 selected from the group consisting of HLA-DRB4, TTC12, GBP4, UBA7, CCDC78, C18orf49, RASEF, TSEN54, RUNX3, PROCR, TGFBR3, PRSS23, CALM1, FAM179A, CCDC114, LGR6, SCAND2, LAIR2, CCL3, CCL3L1, CCL3L3, LAG3, CCL2, OASL, UTS2, LOC100132181 and ALS2CR11, is correlative with or indicates that the patient suffers from or is at risk of developing non-lacunar stroke. Similarly, an increased expression level of one or more lacunar stroke-associated biomarkers of Table 4 selected from the group consisting of STK4, LRRC8B, PDXDC1, LOC254128, IL8, GTF2H2, UGCG, MPZL3, VAPA, STX7, FAM70B, QKI, CHML, FLJ13773, HLA-DQA1 is correlative with or indicates that the patient suffers from or is at risk of developing non-lacunar stroke.

The overexpression or the underexpression of the biomarkers are determined with reference to a control level of expression. The control level of expression can be determined using any method known in the art. For example, the control level of expression can be from a population of individuals known to not have or be at risk for an ischemic event such as lacunar stroke or can be determined with reference to a panel of stably expressed reference biomarkers. Also, threshold levels of expression can be determined based on levels of expression in predetermined populations (e.g., known to not have or be at risk for an ischemic event such as lacunar stroke versus known to have or be at risk for lacunar stroke). Overexpression or underexpression of a plurality of biomarkers from Table 3 or Table 4 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, or more, in comparison to the expression levels of a plurality of stably expressed endogenous reference biomarkers, e.g., those listed in Table 1, is correlative with or indicates that the subject has experienced or is at risk of experiencing a lacunar stroke. Overexpression or underexpression of a plurality of biomarkers from Table 3 or Table 4 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, or more, in comparison to the expression level of the same biomarker in an individual or a population of individuals who have not experienced a vascular event is correlative with or indicates that the subject has experienced or is at risk of experiencing a lacunar stroke.

4. Biomarkers Useful for the Diagnosis of Cause of Non-Lacunar Stroke

In some embodiments, it may be determined that the suspected ischemic event or SDI, or risk thereof, is due to non-lacunar causes. Accordingly, in some embodiments, the biological sample may be tested for expression levels of biomarkers useful for distinguishing lacunar stroke from non-lacunar stroke, as well as for expression levels of biomarkers useful for the determination of the cause of ischemic stroke, particularly non-lacunar stroke. Measuring the expression levels of biomarkers to diagnose the cause of non-lacunar stroke can be performed concurrently with (i.e., in parallel) or sequentially to measuring the expression levels of biomarkers to distinguish the cause of stroke as lacunar or non-lacunar.

Biomarkers useful for the determination and diagnosis of the cause of stroke are described, e.g., in co-owned Application Nos. 61/364,334 and 61/364,449, the disclosures of both of which are hereby incorporated herein by reference in their entirety for all purposes. In addition to evaluating the expression levels of a plurality of biomarkers useful for distinguishing lacunar from non-lacunar stroke, the expression levels of a plurality of biomarkers can be measured to determine whether a suspected or predicted ischemic event is cardioembolic or atherosclerotic. Furthermore, the expression levels of a plurality of biomarkers can be measured to determine if the cause of stroke is due to carotid stenosis, atrial fibrillation or transient ischemic attacks. Classification of stroke subtypes is known in the art and reviewed in, e.g., in Amarenco, et al., *Cerebrovasc Dis* (2009) 27:493-501. Accordingly, in some embodiments, the expression levels of at least about 3, 5, 10, 15, 20, 25, 30, 40, 50, 60, 70, 80, 85 or more, ischemic stroke-associated biomarkers are independently determined. In some embodiments, the expression levels of all ischemic stroke-associated biomarkers in a panel are determined.

Overexpression or underexpression of a plurality of ischemic-stroke-associated biomarkers that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 1, is correlative with or indicates that the subject has experienced or is at risk of experiencing ischemic stroke. Overexpression or underexpression of a plurality of biomarkers that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression level of the same biomarker in an individual or a population of individuals who have not experienced a vascular or ischemic event is correlative with or indicates that the subject has experienced or is at risk of experiencing ischemic stroke.

In various embodiments, the expression levels of a plurality of lacunar stroke associated gene are co-determined together with the expression levels of a plurality of genes useful in the determination of whether a patient has experienced or has a predisposition to experience cardioembolic stroke (a.k.a., cardiac embolism, cardioembolism emboligenic heart disease). A cardioembolic stroke occurs when a thrombus (clot) dislodges from the heart, travels through the cardiovascular system and lodges in the brain, first cutting off the blood supply and then often causing a hemorrhagic bleed. In some embodiments an increased expression level of one or more ischemic stroke-associated biomarkers selected from the group consisting of IRF6 (NM_006147), ZNF254 (NM_203282), GRM5 (NM_000842///NM_001143831), EXT2 (NM_000401///NM_207122), AP3S2 (NM_005829///NR_023361), PIK3C2B (NM_002646), ARHGEF5 (NM_005435), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), PTPN20A///PTPN20B (NM_001042357///NM_001042358///NM_001042359///NM_001042360///NM_001042361///NM_001042362///NM_001042363///NM_001042364///NM_001042365///NM_001042387///NM_001042389///NM_001042390///NM_001042391///NM_001042392///NM_001042393///NM_001042394///NM_001042395///NM_001042396///NM_001042397///NM_015605), LHFP (NM_005780), BANK1 (NM_001083907///NM_001127507///NM_017935), HLA-DOA (NM_002119), EBF1 (NM_024007), TMEM19 (NM_018279), LHFP (NM_005780), FCRL1 (NM_001159397///NM_001159398///NM_052938), OOEP (NM_001080507) and LRRC37A3 (NM_199340) is correlative with or indicates that the patient has experienced or is at risk for cardioembolic stroke. In some embodiments, a decreased expression level of one or more ischemic stroke-associated biomarkers selected from the group consisting of LOC284751 (NM_001025463), CD46 (NM_002389///NM_153826///NM_172350///NM_172351///NM_172352///NM_172353///NM_172354///NM_172355///NM_172356///NM_172357///NM_172358///NM_172359///NM_172360///NM_172361), ENPP2 (NM_001040092///NM_001130863///NM_006209), C19orf28 (NM_001042680///NM_021731///NM_174983), TSKS (NM_021733), CHURC1 (NM_145165), ADAMTSL4 (NM_019032///NM_025008), FLJ40125 (NM_001080401), CLEC18A (NM_001136214///NM_182619), ARHGEF12 (NM_015313), C16orf68 (NM_024109), TFDP1 (NM_007111///NR_026580) and GSTK1 (NM_001143679///NM_001143680///NM_001143681///NM_015917) is correlative with or indicates that the patient has experienced or is at risk for cardioembolic stroke.

In various embodiments, the expression levels of a plurality of lacunar stroke associated gene are co-determined together with the expression levels of a plurality of genes useful in the determination of whether a patient has experienced or has a predisposition to experience carotid stenosis. Carotid stenosis is a narrowing or constriction of the inner surface (lumen) of the carotid artery, usually caused by atherosclerosis. An inflammatory buildup of plaque can narrow the carotid artery and can be a source of embolization. Emboli break off from the plaque and travel through the circulation to blood vessels in the brain, causing ischemia that can either be temporary (e.g., a transient ischemic attack), or permanent resulting in a thromboembolic stroke (a.k.a., atherothrombosis, large-artery atherosclerosis, atherosclerosis with stenosis). In some embodiments, an increased expression level of one or more ischemic stroke-associated biomarkers selected from the group consisting of NT5E (NM_002526), CLASP2 (NM_015097), GRM5 (NM_000842///NM_001143831), PROCR (NM_006404), ARHGEF5 (NM_005435), AKR1C3 (NM_003739), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), LHFP (NM_005780), RNF7 (NM_014245///NM_183237), CYTH3 (NM_004227), EBF1 (NM_024007), RANBP10 (NM_020850), PRSS35 (NM_153362), C12orf42 (NM_001099336///NM_198521) and LOC100127980 (XM_001720119///XM_001722650) is correlative with or indicates that the patient has experienced or is at risk for carotid stenosis. In some embodiments, a decreased expression level of one or more ischemic stroke-associated biomarkers selected from the group consisting of FLJ31945 (XM_001714983///XM_001716811///XM_001718431), LOC284751 (NM_001025463), LOC100271832 (NR_027097), MTBP (NM_022045), ICAM4 (NM_001039132///NM_001544///NM_022377), SHOX2 (NM_001163678///NM_003030///NM_006884), DOPEY2 (NM_005128), CMBL (NM_138809), LOC146880 (NR_026899///NR_027487), SLC20A1 (NM_005415), SLC6A19 (NM_001003841), ARHGEF12 (NM_015313), C16orf68 (NM_024109), GIPC2 (NM_017655) and LOC100144603 (NR_021492) is correlative with or indicates that the patient has experienced or is at risk for carotid stenosis.

In various embodiments, the expression levels of a plurality of lacunar stroke associated gene are co-determined together with the expression levels of a plurality of genes useful in the determination of whether a patient has experienced or has a predisposition to experience atrial fibrillation. Atrial fibrillation (AF or A-fib) is the most common cardiac arrhythmia and involves the two upper chambers (atria) of the heart fibrillating (i.e., quivering) instead of a coordinated contraction. In some instances, cardioembolic stroke can occur as a result of atrial fibrillation. Cardioembolic stroke can be a downstream result of atrial fibrillation in that stagnant blood in the fibrillating atrium can form a thrombus that then embolises to the cerebral circulation, blocking arterial blood flow and causing ischaemic injury. In some embodiments, an increased expression level of one or more ischemic stroke-associated biomarkers selected from the group consisting of SMC1A (NM_006306), SNORA68 (NR_000012), GRLF1 (NM_004491), SDC4 (NM_002999), HIPK2 (NM_001113239///NM_022740///XM_001716827///XM_925800), LOC100129034 (NR_027406///XR_079577), CMTM1 (NM_052999///NM_181268///NM_181269///NM_181270///NM_181271///NM_181272///NM_181283///NM_181296) and TTC7A (NM_020458) is correlative with or indicates that the patient has experienced or is at risk for atrial fibrillation. In some embodiments, a decreased expression level of one or more ischemic stroke-associated biomarkers selected from the group consisting of LRRC43 (NM_001098519///NM_152759), MIF///SLC2A11 (NM_001024938///NM_001024939///NM_002415///NM_030807), PER3 (NM_016831), PPIE (NM_006112///NM_203456///NM_203457), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), DUSP16 (NM_030640), BRUNOL6 (NM_052840), GPR176 (NM_007223), C6orf164 (NR_026784) and MAP3K7IP1 (NM_006116///NM_153497) is correlative with or indicates that the patient has experienced or is at risk for atrial fibrillation.

In various embodiments, the expression levels of a plurality of lacunar stroke associated gene are co-determined together with the expression levels of a plurality of genes useful in the determination of whether a patient has experienced or has a predisposition to experience transient ischemic attacks (TIA). A transient ischemic attack is a change in the blood supply to a particular area of the brain, resulting in brief neurologic dysfunction that persists, by definition, for less than 24 hours. If symptoms persist longer, then it is categorized as a stroke. In some embodiments, an increased expression level of one or more TIA-associated biomarkers selected from the group consisting of GABRB2 (NM_000813///NM_021911), ELAVL3 (NM_001420///NM_032281), COL1A1 (NM_000088), SHOX2 (NM_003030///NM_006884), TWIST1 (NM_000474), DPPA4 (NM_018189), DKFZP434P211 (NR_003714), WIT1 (NM_015855///NR_023920), SOX9 (NM_000346), DLX6 (NM_005222), ANXA3 (NM_005139), EPHA3 (NM_005233///NM_182644), SOX11 (NM_003108), SLC26A8 (NM_052961///NM_138718), CCRL1 (NM_016557///NM_178445), FREM2 (NM_207361), STOX2 (NM_020225), ZNF479 (NM_033273///XM_001714591///XM_001719979), LOC338862 (NR_038878.1), ASTN2 (NM_014010///NM_198186///NM_198187///NM_198188), FOLH1 (NM_001014986///NM_004476), SNX31 (NM_152628), KREMEN1 (NM_001039570///NM_001039571), ALS2CR11 (NM_152525), FIGN (NM_018086), RORB (NM_006914), LOC732096 (XM_001720784///XM_001725388///XR_016064), GYPA (NM_002099), ALPL (NM_000478///NM_001127501), LHX2 (NM_004789), GALNT5 (NM_014568), SRD5A2L2 (NM_001010874), GALNT14 (NM_024572), OVOL2 (NM_021220), BMPR1B (NM_001203), UNC5B (NM_170744), ODZ2 (NM_001080428///NM_001122679), RASAL2 (NM_004841///NM_170692), SHOX (NM_000451///NM_006883), C19orf59 (NM_174918), ZNF114 (NM_153608), SRGAP1 (NM_020762), ELAVL2 (NM_004432), NCRNA00032 (XM_376821///XM_938938), LOC440345 (XR_015786), FLJ30375 (XM_001724993///XM_001725199///XM_001725628), TFPI (NM_001032281///NM_006287), PTGR1 (NM_012212), ROBOT (NM_002941///NM_133631), NR2F2 (NM_021005), GRM5 (NM_000842///NM_001143831), LUM (NM_002345), FLJ39051 (NR_033839.1), COL1A2 (NM_000089), CASP5 (NM_001136109///NM_001136110///NM_001136111///NM_001136112///NM_004347//), OPCML (NM_001012393///NM_002545), TTC6 (NM_001007795), TFAP2B (NM_003221), CRISP2 (NM_001142407///NM_001142408///NM_001142417///NM_001142435///NM_003296), SOX11 (NM_003108), ANKRD30B (XM_001716904///XM_001717561///XM_001717810), SCN2A (NM_001040142///NM_001040143///NM_021007), MYNN (NM_018657), FOXA2 (NM_021784///NM_153675), DKFZP434B061 (XR_015528///XR_040812), LOC645323 (NR_015436///NR_024383///NR_024384///XR_041118///XR_041119///XR_041120), SNIP (NM_025248), LOC374491 (NR_002815), ADAM30 (NM_021794), SIX3 (NM_005413), FLJ36144 (XR_040632///XR_040633///XR_040634), CARD8 (NM_014959), RP1-127L4.6 (NM_001010859), FAM149A (NM_001006655///NM_015398), B3GAT2 (NM_080742), SPOCK3 (NM_001040159///NM_016950), ITGBL1 (NM_004791), IQGAP3 (NM_178229), C7orf45 (NM_145268), ZNF608 (NM_020747), LOC375010 (XR_041271), LRP2 (NM_004525), TGFB2 (NM_001135599///NM_003238), SHOX2 (NM_003030///NM_006884), HOXC4///HOXC6 (NM_004503///NM_014620///NM_153633///NM_153693), ELTD1 (NM_022159), FAM182B///RP13-401N8.2 (XM_001132551///XM_001133521///XM_001718365///XM_933752), LIFR (NM_001127671///NM_002310), FOLH1 (NM_001014986///NM_004476), EHF (NM_012153), NDST3 (NM_004784), BRUNOL5 (NM_021938), LOC728460 (XM_001128581///XM_001129498///XM_001723364), PDE1A (NM_001003683///NM_005019), POU2AF1

(NM_006235), FAT1 (NM_005245), PCDH11X///PCDH11Y (NM_014522///NM_032967///NM_032968///NM_032969///NM_032971///NM_032972), FLJ37786 (XR_041472///XR_041473), SLC22A4 (NM_003059), DHRS13 (NM_144683), MEG3 (NR_002766///NR_003530///NR_003531), PIWIL1 (NM_004764), LOC203274 (AL117607.1///BC080605.1), LOC100133920///LOC286297 (NR_024443///XM_001714612///XM_372109///XM_933054///XM_933058), DMRT1 (NM_021951), ADM (NM_001124), VWA3B (NM_144992), GAFA3 (XM_001715321///XM_001722922///XM_001723636), HESX1 (NM_003865), ADAMDEC1 (NM_014479), CAV1 (NM_001753), LAMB4 (NM_007356), TPTE (NM_199259///NM_199260///NM_199261), PPP1R1C (NM_001080545), HPSE (NM_001098540///NM_006665), AIM2 (NM_004833), RUNDC3B (NM_001134405///NM_001134406///NM_138290), CARD16 (NM_001017534///NM_052889), FAM124A (NM_145019), MGC39584 (XR_017735///XR_017787///XR_041937), OSM (NM_020530), RFX2 (NM_000635///NM_134433), MYBPC1 (NM_002465///NM_206819///NM_206820///NM_206821), LTBR (NM_002342), C18orf2 (NM_031416///NR_023925///NR_023926///NR_023927///NR_023928), SNRPN (NM_003097///NM_022805///NM_022806///NM_022807///NM_022808///NR_001289), FLJ36031 (NM_175884), IL1B (NM_000576), TRPM1 (NM_002420), OSTCL (NM_145303), MAPK14 (NM_001315///NM_139012///NM_139013///NM_139014), KCNJ15///LOC100131955 (NM_002243///NM_170736///NM_170737///XM_001713900///XM_001715532///XM_0), FIGN (NM_018086), HNT (NM_001048209///NM_016522), S100A12 (NM_005621), CHIT1 (NM_003465), C7orf53 (NM_001134468///NM_182597), FAM13A1 (NM_001015045///NM_014883), GNAO1 (NM_020988///NM_138736), MAPK14 (NM_001315///NM_139012///NM_139013///NM_139014), FAM55D (NM_001077639///NM_017678), PRKD2 (NM_001079880///NM_001079881///NM_001079882///NM_016457), LIMK2 (NM_001031801///NM_005569///NM_016733), C18orf54 (NM_173529), IGFBP5 (NM_000599), EVI1 (NM_001105077///NM_001105078///NM_005241), PLSCR1 (NM_021105), FOXC1 (NM_001453), LOC646627 (NM_001085474), ZNF462 (NM_021224), CNTLN (NM_001114395///NM_017738), ZNF438 (NM_001143766///NM_001143767///NM_001143768///NM_001143769///NM_001143770), DEFB105A///DEFB105B (NM_001040703///NM_152250), LOC340017 (NR_026992.1), C1orf67 (NM_144989), ACSL1 (NM_001995), ADH1B (NM_000668), SLC2A14///SLC2A3 (NM_006931///NM_153449), IL1B (NM_000576), ST3GAL4 (NM_006278///XM_001714343///XM_001726541///XM_001726562), UBE2J1 (NM_016021), PNPLA3 (NM_025225) and PAPPA (NM_002581) is correlative with or indicates that the patient has experienced or is at risk for TIA. In some embodiments, a decreased expression level of one or more TIA-associated biomarkers selected from the group consisting of NBPF10///RP11-94I2.2 (NM_001039703///NM_183372///XM_001722184), SFXN1 (NM_022754), SPIN3 (NM_001010862), UNC84A (NM_001130965///NM_025154), OLFM2 (NM_058164), PPM1K (NM_152542), P2RY10 (NM_014499///NM_198333), ZNF512B (NM_020713), MORF4L2 (NM_001142418///NM_001142419///NM_001142420///NM_001142421///NM_001142422), GIGYF2 (NM_001103146///NM_001103147///NM_001103148///NM_015575), ERAP2 (NM_001130140///NM_022350), SLFN13 (NM_144682), LOC401431 (XR_040272///XR_040273///XR_040274///XR_040275), MED6 (NM_005466), BAIAP2L1///LOC100128461 (NM_018842///XM_001722656///XM_001724217///XM_001724858), LNPEP (NM_005575///NM_175920), MBNL1 (NM_021038///NM_207292///NM_207293///NM_207294///NM_207295///NM_207296), NOS3 (NM_000603), MCF2L (NM_001112732///NM_024979), KIAA1659 (XM_001723799///XM_001725435///XM_001726785), SCAMP5 (NM_138967), LOC648921 (XM_001715629///XM_001720571///XR_018520), ANAPC5 (NM_001137559///NM_016237), SPON1 (NM_006108), FUS (NM_004960), GPR22 (NM_005295), GAL3ST4 (NM_024637), METTL3 (NM_019852), LOC100131096 (XM_001720907///XM_001726205///XM_001726705), FAAH2 (NM_174912), SMURF2 (NM_022739), SNRPN (NM_003097///NM_022805///NM_022806///NM_022807///NM_022808///NR_001289), FBLN7 (NM_001128165///NM_153214), GLS (NM_014905), G3BP1 (NM_005754///NM_198395), RCAN3 (NM_013441), EPHX2 (NM_001979), DIP2C (NM_014974), CCDC141 (NM_173648), CLTC (NM_004859), FOSB (NM_001114171///NM_006732), CACNA1I (NM_001003406///NM_021096), UNQ6228 (XM_001725293///XM_001725359///XM_001726164), ATG9B (NM_173681), AK5 (NM_012093///NM_174858), RBM14 (NM_006328), MAN1C1 (NM_020379), HELLS (NM_018063), EDAR (NM_022336), SLC3A1 (NM_000341), ZNF519 (NM_145287), LOC100130070///LOC100130775///LOC100131787///LOC100131905///LOC100132291///LOC100132488///RPS27 (NM_001030///XM_001721002///XM_001722161///XM_001722965///XM_001723889//), ZC3H12B (NM_001010888), IQGAP2 (NM_006633), SOX8 (NM_014587), WHDC1L2 (XM_926785), TNPO1 (NM_002270///NM_153188), TNFRSF21 (NM_014452), TSHZ2 (NM_173485), DMRTC1///DMRTC1B (NM_001080851///NM_033053), GSTM1 (NM_000561///NM_146421), GSTM2 (NM_000848///NM_001142368), PNMA6A (NM_032882), CAND1 (NM_018448), CCND3 (NM_001136017///NM_001136125///NM_001136126///NM_001760), GSTM1 (NM_000561///NM_146421), and GUSBL2 (NR_003660///XR_042150///XR_042151) is correlative with or indicates that the patient has experienced or is at risk for TIA.

5. Comparison to a Control Level of Expression

The expression levels of the lacunar stroke-associated biomarkers are compared to a control level of expression. As appropriate, the control level of expression can be the expression level of the same lacunar stroke-associated biomarker in an otherwise healthy individual (e.g., in an individual who has not experienced and/or is not at risk of experiencing a vascular event, e.g., TIA, ischemic stroke or a small deep infarct). In some embodiments, the control level of expression is the expression level of a plurality of stably expressed endogenous reference biomarkers, as described herein and/or known in the art. In some embodiments, the control level of expression is a predetermined threshold level of expression of the same lacunar stroke-associated biomarker, e.g., based on the expression level of the biomarker in a population of otherwise healthy individuals. In some embodiments, the expression level of the lacunar stroke-associated biomarker in the test subject and the expression level of the lacunar stroke-associated biomarker in an otherwise healthy individual are normalized to (i.e., divided by), e.g., the expression levels of a plurality of stably expressed endogenous reference biomarkers.

In some embodiments, the overexpression or underexpression of a lacunar stroke associated biomarker is determined with reference to the expression of the same lacunar stroke associated biomarker in an otherwise healthy individual. For example, a healthy or normal control individual has not experienced and/or is not at risk of experiencing ischemic stroke, transient ischemic attack or a small deep infarction. The healthy or normal control individual generally has not experienced a vascular event (e.g., TIA, ischemic stroke, myocardial infarction, peripheral vascular disease, or venous thromboembolism) and does not have cerebral vascular disease. The healthy or normal control individual generally does not have one or more vascular risk factors (e.g., hypertension, diabetes mellitus, hyperlipidemia, or tobacco smoking). As appropriate, the expression levels of the target lacunar stroke-associated biomarker in the healthy or normal control individual can be normalized (i.e., divided by) the expression levels of a plurality of stably expressed endogenous reference biomarkers.

In some embodiments, the overexpression or underexpression of a lacunar stroke associated biomarker is determined with reference to one or more stably expressed endogenous reference biomarkers. Internal control biomarkers or endogenous reference biomarkers are expressed at the same or nearly the same expression levels in the blood of patients with stroke or TIAs or SDIs as compared to control patients. Target biomarkers are expressed at higher or lower levels in the blood of the stroke or TIA or SDI patients. The expression levels of the target biomarker to the reference biomarker are normalized by dividing the expression level of the target biomarker to the expression levels of a plurality of endogenous reference biomarkers. The normalized expression level of a target biomarker can be used to predict the occurrence or lack thereof of stroke or TIA or SDI, and/or the cause of stroke or TIA or SDI.

In some embodiments, the expression level of the lacunar stroke-associated biomarker from a patient suspected of having or experiencing lacunar stroke and from a control patient are normalized with respect to the expression levels of a plurality of stably expressed endogenous genes. The expression levels of the normalized expression of the lacunar stroke-associated biomarker can be compared to the expression levels of the normalized expression of the same lacunar stroke-associated biomarker in a control patient. The determined fold change in expression=normalized expression of target biomarker in lacunar stroke patient/normalized expression of target biomarker in control patient. Overexpression or underexpression of the normalized lacunar stroke-associated biomarker in the lacunar stroke patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of the normalized lacunar stroke-associated biomarker in a healthy control patient is correlative with or indicates that the lacunar stroke or SDI patient has experienced or is at risk of experiencing lacunar stroke.

In some embodiments, the control level of expression is a predetermined threshold level. The threshold level can correspond to the level of expression of the same lacunar stroke-associated biomarker in an otherwise healthy individual or a population of otherwise healthy individuals, optionally normalized to the expression levels of a plurality of endogenous reference biomarkers. After expression levels and normalized expression levels of the lacunar stroke-associated biomarkers are determined in a representative number of otherwise healthy individuals and individuals predisposed to experiencing SDI or lacunar stroke, normal and lacunar stroke expression levels of the lacunar stroke-associated biomarkers can be maintained in a database, allowing for determination of threshold expression levels indicative of the presence or absence of risk to experience lacunar stroke or the occurrence of lacunar stroke. If the predetermined threshold level of expression is with respect to a population of normal control patients, then overexpression or underexpression of the lacunar stroke-associated biomarker (usually normalized) in the stroke patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the threshold level is correlative with or indicates that the lacunar stroke patient has experienced or is at risk of experiencing lacunar stroke. If the predetermined threshold level of expression is with respect to a population of patients known to have experienced lacunar stroke or known to be at risk for experiencing lacunar stroke, then an expression level in the patient suspected of experiencing lacunar stroke that is approximately equal to the threshold level (or overexpressed or underexpressed greater than the threshold level of expression), is correlative with or indicates that the lacunar stroke or SDI patient has experienced or is at risk of experiencing lacunar stroke.

With respect to the endogenous reference biomarkers used for comparison, preferably, Exemplary endogenous reference biomarkers that find use are listed in Table 1, below. Further suitable endogenous reference biomarkers are published, e.g., in Stamova, et al., BMC Medical Genomics (2009) 2:49. In some embodiments, the expression levels of a plurality of endogenous reference biomarkers are determined as a control. In some embodiments, the expression levels of at least about 2, 3, 4, 5, 6, 7, 8, 9, 10, 15, 20, 25, 30, 35, or more, endogenous reference biomarkers, e.g., as listed in Table 1 or known in the art, are determined as a control.

TABLE 1

The 38 endogenous reference biomarkers stably expressed in blood for use in normalization and as control levels.
Table 1. Stably expressed endogenous reference biomarkers

| Probe Set ID | Gene Symbol | Gene Title | GenBank ID | UniGene ID | RefSeq Transcript ID | RefSeq Protein ID |
|---|---|---|---|---|---|---|
| 201499_s_at | USP7 | ubiquitin specific peptidase 7 (herpes virus-associated) | NM_003470.1 | Hs.706830 | NM_003470 | NP_003461 |
| 202501_at | MAPRE2 | microtubule-associated protein, RP/EB family, member 2 | NM_014268.1 | Hs.532824 | NM_001143826 /// NM_001143827 /// NM_014268 /// NR_026570 | NP_001137298 /// NP_001137299 /// NP_055083 |

TABLE 1-continued

The 38 endogenous reference biomarkers stably expressed
in blood for use in normalization and as control levels.
Table 1. Stably expressed endogenous reference biomarkers

| Probe Set ID | Gene Symbol | Gene Title | GenBank ID | UniGene ID | RefSeq Transcript ID | RefSeq Protein ID |
|---|---|---|---|---|---|---|
| 202573_at | CSNK1G2 | casein kinase 1, gamma 2 | AL530441 | Hs.651905 | NM_001319 | NP_001310 |
| 203280_at | SAFB2 | scaffold attachment factor B2 | NM_014649.1 | Hs.655392 | NM_014649 | NP_055464 |
| 204842_x_at | PRKAR2A | protein kinase, cAMP-dependent, regulatory, type II, alpha | BC002763.1 | Hs.631923 | NM_004157 | NP_004148 |
| 206138_s_at | PI4KB | phosphatidylinositol 4-kinase, catalytic, beta | NM_002651.1 | Hs.632465 | NM_002651 | NP_002642 |
| 207159_x_at | CRTC1 | CREB regulated transcription coactivator 1 | NM_025021.1 | Hs.371096 | NM_001098482 /// NM_015321 | NP_001091952 /// NP_056136 |
| 208630_at | HADHA | hydroxyacyl-Coenzyme A dehydrogenase/3-ketoacyl-Coenzyme A thiolase/enoyl-Coenzyme A hydratase (trifunctional protein), alpha subunit | AI972144 | Hs.516032 | NM_000182 | NP_000173 |
| 208786_s_at | MAP1LC3B | microtubule-associated protein 1 light chain 3 beta | AF183417.1 | Hs.356061 | NM_022818 | NP_073729 |
| 209192_x_at | KAT5 | K(lysine) acetyltransferase 5 | BC000166.2 | Hs.397010 | NM_006388 /// NM_182709 /// NM_182710 | NP_006379 /// NP_874368 /// NP_874369 |
| 210474_s_at | CDC2L1 /// CDC2L2 | cell division cycle 2-like 1 (PITSLRE proteins) /// cell division cycle 2-like 2 (PITSLRE proteins) | U04819.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 211040_x_at | GTSE1 | G-2 and S-phase expressed 1 | BC006325.1 | Hs.386189 | NM_016426 | NP_057510 |
| 211289_x_at | CDC2L1 /// CDC2L2 | cell division cycle 2-like 1 (PITSLRE proteins) /// cell division cycle 2-like 2 (PITSLRE proteins) | AF067524.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 213311_s_at | TCF25 | transcription factor 25 (basic helix-loop-helix) | BF000251 | Hs.415342 | NM_014972 | NP_055787 |
| 214665_s_at | CHP | calcium binding protein P22 | AK000095.1 | Hs.406234 | NM_007236 | NP_009167 |
| 215063_x_at | LRRC40 | leucine rich repeat containing 40 | AL390149.1 | Hs.147836 | NM_017768 | NP_060238 |
| 215200_x_at | — | — | AK022362.1 | Hs.663419 | — | — |
| 215568_x_at | hCG_2003956 /// LYPLA2 /// LYPLA2P1 | hCG2003956 /// lysophospholipase II /// lysophospholipase II pseudogene 1 | AL031295 | Hs.533479 | NM_007260 /// NR_001444 | NP_009191 |
| 216038_x_at | DAXX | death-domain associated protein | BE965715 | Hs.336916 | NM_001141969 /// NM_001141970 /// NM_001350 /// NR_024517 | NP_001135441 /// NP_001135442 /// NP_001341 |
| 217393_x_at | UBE2NL | ubiquitin-conjugating enzyme E2N-like | AL109622 | Hs.585177 | NM_001012989 | NP_001013007 |
| 217549_at | — | — | AW574933 | Hs.527860 | — | — |
| 217672_x_at | EIF1 | eukaryotic translation initiation factor 1 | BF114906 | Hs.150580 | NM_005801 | NP_005792 |
| 217938_s_at | KCMF1 | potassium channel modulatory factor 1 | NM_020122.1 | Hs.654968 | NM_020122 | NP_064507 |
| 218378_s_at | PRKRIP1 | PRKR interacting protein 1 (IL11 inducible) | NM_024653.1 | Hs.406395 | NM_024653 | NP_078929 |
| 218571_s_at | CHMP4A | chromatin modifying protein 4A | NM_014169.1 | Hs.279761 | NM_014169 | NP_054888 |
| 219074_at | TMEM184C | transmembrane protein 184C | NM_018241.1 | Hs.203896 | NM_018241 | NP_060711 |
| 220052_s_at | TINF2 | TERF1 (TRF1)-interacting nuclear factor 2 | NM_012461.1 | Hs.496191 | NM_001099274 /// NM_012461 | NP_001092744 /// NP_036593 |
| 220411_x_at | PODNL1 | podocan-like 1 | NM_024825.1 | Hs.448497 | NM_001146254 /// NM_001146255 /// NM_024825 | NP_001139726 /// NP_001139727 /// NP_079101 |

TABLE 1-continued

The 38 endogenous reference biomarkers stably expressed
in blood for use in normalization and as control levels.
Table 1. Stably expressed endogenous reference biomarkers

| Probe Set ID | Gene Symbol | Gene Title | GenBank ID | UniGene ID | RefSeq Transcript ID | RefSeq Protein ID |
|---|---|---|---|---|---|---|
| 221813_at | FBXO42 | F-box protein 42 | AI129395 | Hs.522384 | NM_018994 | NP_061867 |
| 222207_x_at | LOC441258 | Williams Beuren syndrome chromosome region 19 pseudogene | AK024602.1 | Hs.711232 | — | — |
| 222733_x_at | RRP1 | ribosomal RNA processing 1 homolog (S. cerevisiae) | BC000380.1 | Hs.110757 | NM_003683 | NP_003674 |
| 224667_x_at | C10orf104 | chromosome 10 open reading frame 104 | AK023981.1 | Hs.426296 | NM_173473 | NP_775744 |
| 224858_at | ZDHHC5 | zinc finger, DHHC-type containing 5 | AK023130.1 | Hs.27239 | NM_015457 | NP_056272 |
| 225403_at | C9orf23 | chromosome 9 open reading frame 23 | AL528391 | Hs.15961 | NM_148178 /// NM_148179 | NP_680544 /// NP_680545 |
| 226253_at | LRRC45 | leucine rich repeat containing 45 | BE965418 | Hs.143774 | NM_144999 | NP_659436 |
| 227651_at | NACC1 | nucleus accumbens associated 1, BEN and BTB (POZ) domain containing | AI498126 | Hs.531614 | NM_052876 | NP_443108 |
| 232190_x_at | LOC100133445 /// LOC115110 | hypothetical LOC100133445 /// hypothetical protein LOC115110 | AI393958 | Hs.132272 | NR_026927 /// XR_036887 /// XR_038144 | — |
| 49878_at | PEX16 | peroxisomal biogenesis factor 16 | AA523441 | Hs.100915 | NM_004813 /// NM_057174 | NP_004804 /// NP_476515 |

In some embodiments, the expression levels of the endogenous reference biomarkers GAPDH, ACTB, B2M, HMBS and PPIB are determined as a control. In some embodiments, the expression levels of 2, 3, 4, 5, 6, 7, 8, 9, 10, 15, 20, 25, or more, endogenous reference biomarkers selected from the group consisting of USP7, MAPRE2, CSNK1G2, SAFB2, PRKAR2A, PI4KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

Biomarkers indicative of lacunar stroke have levels of expression that are at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., the geometric average expression level of the evaluated endogenous reference biomarkers, e.g., 2, 3, 4, 5, 6, 7, 8, 9, 10, 15, 20, 25, 30, 35, or more biomarkers listed in Table 1.

6. Methods of Detecting Biomarkers

Gene expression may be measured using any method known in the art. One of skill in the art will appreciate that the means of measuring gene expression is not a critical aspect of the invention. The expression levels of the biomarkers can be detected at the transcriptional or translational (i.e., protein) level.

In some embodiments, the expression levels of the biomarkers are detected at the transcriptional level. A variety of methods of specific DNA and RNA measurement using nucleic acid hybridization techniques are known to those of skill in the art (see, Sambrook, supra and Ausubel, supra) and may be used to detect the expression of the genes set forth in Tables 3 and 4. Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention. All forms of RNA can be detected, including, e.g., message RNA (mRNA), microRNA (miRNA), ribosomal RNA (rRNA) and transfer RNA (tRNA).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins Nucleic Acid Hybridization, A Practical Approach, IRL Press (1985); Gall and Pardue, Proc. Natl. Acad. Sci. U.S.A., 63:378-383 (1969); and John et al. Nature, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "Practice and Theory of Enzyme Immunoassays," Laboratory Techniques in Biochemistry and Molecular Biology, Burdon and van Knippenberg Eds., Elsevier (1985), pp. 9-20).

The probes can be labeled either directly, e.g., with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^{3}$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden Introduction to Immunocytochemistry, 2nd ed., Springer Verlag, N Y (1997); and in Haugland Handbook of Fluorescent Probes and Research Chemicals, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

For example, in one embodiment of the invention, microarrays are used to detect the pattern of gene expression. Microarrays provide one method for the simultaneous measurement of the expression levels of large numbers of genes. Each array consists of a reproducible pattern of a plurality of nucleic acids (e.g., a plurality of nucleic acids that hybridize to a plurality of the genes set forth in Tables 3 and 4) attached to a solid support. In one embodiment, the array contains a plurality of nucleic acids that hybridize to a plurality of the genes listed in Table 3. In one embodiment, the array contains a plurality of nucleic acids that hybridize to a plurality of the genes listed in Table 4. In one embodiment, the array further contains a plurality of nucleic acids that hybridize to a plurality of genes useful for diagnosing ischemic stroke, cardioembolic stroke, carotid stenosis, atrial fibrillation or transient ischemic attacks, as described herein or known in the art. Labeled RNA or DNA is hybridized to complementary probes on the array and then detected by laser scanning. Hybridization intensities for each probe on the array are determined and converted to a quantitative read-out of relative gene expression levels in ischemia (e.g., stroke or SDI (lacunar or non-lacunar) or transient ischemic attacks).

In some embodiments, a sample is obtained from a subject, total mRNA is isolated from the sample and is converted to labeled cRNA and then hybridized to an array. Relative transcript levels are calculated by reference to appropriate controls present on the array and in the sample. See Mahadevappa and Warrington, Nat. Biotechnol. 17, 1134-1136 (1999).

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) Science, 251: 767-777; Sheldon et al. (1993) Clinical Chemistry 39(4): 718-719, and Kozal et al. (1996) Nature Medicine 2(7): 753-759. Integrated microfluidic systems and other point-of-care diagnostic devices available in the art also find use. See, e.g., Liu and Mathies, Trends Biotechnol. (2009) 27(10):572-81 and Tothill, Semin Cell Dev Biol (2009) 20(1):55-62. Microfluidics systems for use in detecting levels of expression of a plurality of nucleic acids are available, e.g., from NanoString Technologies, on the internet at nanostring.com.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) Analytical Biochemistry 181: 153-162; Bogulayski (1986) et al. J. Immunol. Methods 89:123-130; Prooijen-Knegt (1982) Exp. Cell Res. 141:397-407; Rudkin (1976) Nature 265:472-473, Stollar (1970) Proc. Nat'l Acad. Sci. USA 65:993-1000; Ballard (1982) Mol. Immunol. 19:793-799; Pisetsky and Caster (1982) Mol. Immunol. 19:645-650; Viscidi et al. (1988) J. Clin. Microbial. 41:199-209; and Kiney et al. (1989) J. Clin. Microbiol. 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) Fundamental Immunology Raven Press, Ltd., NY (1993); Coligan, et al., Current Protocols in Immunology, Wiley Interscience (1991-2008); Harlow and Lane, Antibodies: A Laboratory Manual Cold Spring Harbor Press, N Y (1988); Harlow and Lane, Using Antibodies, Cold Spring Harbor Press, N Y (1999); Stites et al. (eds.) Basic and Clinical Immunology (4th ed.) Lange Medical Publications, Los Altos, Calif., and references cited therein; Goding Monoclonal Antibodies: Principles and Practice (2d ed.) Academic Press, New York, N.Y., (1986); and Kohler and Milstein Nature 256: 495-497 (1975)). Other suitable techniques for antibody preparation include selection of libraries of recombinant antibodies in phage or similar vectors (see, Huse et al. Science 246:1275-1281 (1989); and Ward et al. Nature 341:544-546 (1989)). Specific monoclonal and polyclonal antibodies and antisera will usually bind with a dissociation constant ($K_D$) of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. High throughput multiplex nucleic acid sequencing or "deep sequencing" to detect captured expressed biomarker genes also finds use. High throughput sequencing techniques are known in the art (e.g., 454 Sequencing on the internet at 454.com).

An alternative means for determining the level of expression of the nucleic acids of the present invention is in situ hybridization. In situ hybridization assays are well known and are generally described in Angerer et al., Methods Enzymol. 152:649-660 (1987). In an in situ hybridization assay, cells, preferentially human cells, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

In other embodiments, quantitative RT-PCR is used to detect the expression of a plurality of the genes set forth in Tables 3 and 4. In one embodiment, quantitative RT-PCR is used to detect a plurality of the genes listed in Table 3. In one embodiment, quantitative RT-PCR is used to detect a plurality of the genes listed in Table 4. In one embodiment, quantitative RT-PCR is used to further detect a plurality of the genes useful for the diagnosis of ischemic stroke, cardioembolic stroke, carotid stenosis, atrial fibrillation and/or transient ischemic attacks, as described herein and known in the art. A general overview of the applicable technology can be found, for example, in A-Z of Quantitative PCR, Bustin, ed., 2004, International University Line; Quantitative PCR Protocols, Kochanowski and Reischl, eds., 1999, Humana Press; Clinical Applications of PCR, Lo, ed., 2006, Humana Press; PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202. Methods for multiplex PCR, known in the art, are applicable to the present invention.

Accordingly, in one embodiment of the invention provides a reaction mixture comprising a plurality of polynucleotides which specifically hybridize (e.g., primers) to a plurality of nucleic acid sequences of the genes set forth in Tables 3 and 4. In some embodiments, the invention provides a reaction mixture comprising a plurality of polynucleotides which specifically hybridize (e.g., primers) to a plurality of nucleic acid sequences of the genes set forth in Table 3. In some embodiments, the invention provides a reaction mixture comprising a plurality of polynucleotides which specifically hybridize (e.g., primers) to a plurality of nucleic acid sequences of the genes set forth in Table 4. In some embodiments, the invention provides a reaction mixture further comprising a plurality of polynucleotides which specifically hybridize (e.g., primers) to a plurality of nucleic acid sequences of the genes useful for the diagnosis of ischemic stroke, cardioembolic stroke, carotid stenosis, atrial fibrillation and/or transient ischemic attacks, as described herein and known in the art. In some embodiments, the reaction mixture is a PCR mixture, for example, a multiplex PCR mixture.

This invention relies on routine techniques in the field of recombinant genetics. Generally, the nomenclature and the laboratory procedures in recombinant DNA technology described below are those well-known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-2008, Wiley Interscience)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

In some embodiments, the expression level of the biomarkers described herein are detected at the translational or protein level. Detection of proteins is well known in the art, and methods for protein detection known in the art find use. Exemplary assays for determining the expression levels of a plurality of proteins include, e.g., ELISA, flow cytometry, mass spectrometry (e.g., MALDI or SELDI), surface plasmon resonance (e.g., BiaCore), microfluidics and other biosensor technologies. See, e.g., Tothill, Semin Cell Dev Biol (2009) 20(1):55-62.

7. Lacunar Stroke and Ischemia Reference Profiles

The invention also provides expression reference profiles useful for the diagnosis of lacunar stroke or for distinguishing lacunar stroke from non-lacunar stroke. The gene expression reference profiles comprise information correlating the expression levels of a plurality of lacunar stroke-associated genes (i.e., a plurality of the genes set forth in Tables 3 and 4) to lacunar stroke (versus non-lacunar stroke). In one embodiment, the lacunar stroke reference profile correlates the expression levels of a plurality of the genes listed in Table 3 to the occurrence or risk of lacunar stroke. In one embodiment, the lacunar stroke reference profile correlates the expression levels of a plurality of the genes listed in Table 4 to the occurrence or risk of lacunar stroke. In one embodiment, the lacunar stroke reference profile correlates the expression levels of a plurality of the genes listed in Table 3 to the occurrence or risk of non-lacunar stroke (e.g., cardioembolic stroke, carotid stenosis, atrial fibrillation, transient ischemic attacks, or other causes). In one embodiment, the lacunar stroke reference profile correlates the expression levels of a plurality of the genes listed in Table 4 to the occurrence or risk of non-lacunar stroke (e.g., cardioembolic stroke, carotid stenosis, atrial fibrillation, transient ischemic attacks, or other causes). The profiles can conveniently be used to diagnose, monitor and prognose the cause of an ischemic event.

One embodiment of the invention provides a lacunar stroke gene expression reference profile for subjects who have experienced or are at risk for experiencing lacunar stroke. Accordingly, the lacunar stroke reference profile correlates the expression levels of a plurality of the genes selected from Table 3. For example, an expression profile exhibiting an increase in expression of a plurality of the following genes: AKAP9, ALS2CR11, BNC2, BZRAP1, C18orf49, CALM1, CCDC114, CCDC78, CCL2, CCL3, CCL3L1, CCL3L3, CCL4, CHST2, CSF1, ERBB2, FAM179A, GBP4, GBR56, GRAMD3, GRHL2, GRK4, HLA-DRB4, ITIH4, KIAA1618, LAG3, LAIR2, LGR6, LOC100132181, LOC147646, LOC150622, LOC161527, OASL, PLEKHF1, PRKD2, PROCR, PRSS23, RASEF, RGNEF, RUNX3, SCAND2, SESN2, SLAMF7, SPON2, STAT1, SYNGR1, TRX21, TGFBR3, TMEM67, TSEN54, TTC12, TUBE1, UBA7, UTS2, and ZNF827, when compared to the control level, and/or a decrease in expression of a plurality of the following genes: AGFG1, BTG1, CFDP1, CHML, CNPY2, FAM105A, FAM70B, FLJ13773, GATM, GTF2H2, GTF2H2B, HLA-DQA1, IGHG1, IL18RAP, IL8, LOC254128, LRRC8B, MPZL3, N4BP2, PDXDC1, PHACTR1, QKI, RTKN2, SLC16A1, SOCS1, SPAG17, ST6GALNAC1, STK17B, STK4, STT3B, STX16, STX7, TBC1D12, TRIM4, UACA, UGCG, VAPA, and WHAMML2, when compared to the control level is a reference profile for a subject who has experienced or is at risk for lacunar stroke.

One embodiment of the invention provides a lacunar stroke gene expression reference profile for subjects who have experienced or are at risk for experiencing lacunar stroke. Accordingly, the lacunar stroke reference profile correlates the expression levels of a plurality of the genes selected from Table 4. For example, an expression profile exhibiting an increase in expression of a plurality of the following genes: HLA-DRB4, TTC12, GBP4, UBA7, CCDC78, C18orf49, RASEF, TSEN54, RUNX3, PROCR, TGFBR3, PRSS23, CALM1, FAM179A, CCDC114, LGR6, SCAND2, LAIR2, CCL3, CCL3L1, CCL3L3, LAG3, CCL2, OASL, UTS2, LOC100132181 and ALS2CR11, when compared to the control level, and/or a decrease in expression of a plurality of the following genes: STK4, LRRC8B, PDXDC1, LOC254128, IL8, GTF2H2, UGCG, MPZL3, VAPA, STX7, FAM70B, QKI, CHML, FLJ13773, HLA-DQA1, when compared to the control level is a reference profile for a subject who has experienced or is at risk for lacunar stroke.

One embodiment of the invention further provides an ischemia reference profile for subjects who have experienced or are at risk for experiencing stroke, regardless of cause. Accordingly, the ischemia reference profile correlates the expression levels of a plurality of ischemic stroke-associated genes. For example, an expression profile exhibiting an increase in expression of a plurality of the following genes: PGM5, CCDC144C///LOC100134159, LECT2, SHOX, TBX5, SNIP, RBMS3, P704P, THSD4, FAT3, SNRPN, GLYATL1, GADL1, CXADR, OVOL2, RNF141, CLEC4E, BXDC5, UNC5B, TIMP2, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, SCD5, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488 and MCTP1 when compared to the control level, and/or a decrease in expression of a plurality of the following genes: SPTLC3, DKRZP434L187, SPIB, HNRNPUL2, FOXA2, RPL22 and SH3GL3 when compared to the control level is a reference profile for a subject who has experienced or is at risk for stroke.

One embodiment of the invention further provides an ischemia reference profile for subjects who have experienced or are at risk for experiencing cardioembolic stroke. Accordingly, the ischemia reference profile correlates the expression levels of a plurality of the genes correlative for or associated with cardioembolic stroke. For example, an expression profile exhibiting an increase in expression of a plurality of the following genes: IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP and LRRC37A3 when compared to the control level, and/or a decrease in expression of a plurality of the following genes: LOC284751, CD46, ENPP2, C19orf28, TSKS, CHURC1, ADAMTSL4, F1140125, CLEC18A, ARHGEF12, C16orf68, TFDP1 and GSTK1 when compared to the control level is a reference profile for a subject who has experienced or is at risk for a cardioembolic stroke.

One embodiment of the invention further provides an ischemia reference profile for subjects who have experienced or are at risk for experiencing carotid stenosis and atherosclerotic stroke. Accordingly, the ischemia reference profile correlates the expression levels of a plurality of the genes correlative for or associated with carotid stenosis and atherosclerotic stroke. For example, an expression profile exhibiting an increase in expression of a plurality of the following genes: NT5E, CLASP2, GRM5, PROCR, ARHGEF5, AKR1C3, COL13A1, LHFP, RNF7, CYTH3, EBF1, RANBP10, PRSS35, C12orf42 and LOC100127980 when compared to the control level, and/or a decrease in expression of a plurality of the following genes: F1131945, LOC284751, LOC100271832, MTBP, ICAM4, SHOX2, DOPEY2, CMBL, LOC146880, SLC20A1, SLC6A19, ARHGEF12, C16orf68, GIPC2 when compared to the control level is a reference profile for a subject who has experienced or is at risk for carotid stenosis and atherothrombotic stroke.

One embodiment of the invention further provides an ischemia reference profile for subjects who have experienced or are at risk for experiencing atrial fibrillation. Accordingly, the ischemia reference profile correlates the expression levels of a plurality of the genes correlative for or associated with atrial fibrillation. For example, an expression profile exhibiting an increase in expression of a plurality of the following genes: SMC1A, SNORA68, GRLF1, SDC4, HIPK2, LOC100129034, CMTM1 and TTC7A when compared to the control level, and/or a decrease in expression of a plurality of the following genes: LRRC43, MIF/// SLC2A11, PER3, PPIE, COL13A1, DUSP16, LOC100129034, BRUNOL6, GPR176, C6orf164 and MAP3K7IP1 when compared to the control level is a reference profile for a subject who has experienced or is at risk for atrial fibrillation.

One embodiment of the invention further provides an ischemia reference profile for subjects who have experienced or are at risk for experiencing transient ischemic attacks. Accordingly, the ischemia reference profile correlates the expression levels of a plurality of the genes correlative for or associated with transient ischemic attacks. For example, an expression profile exhibiting an increase in expression of a plurality of the following genes: GABRB2, ELAVL3, COL1A1, SHOX2, GABRB2, TWIST1, DPPA4, DKFZP434P211, WIT1, SOX9, DLX6, ANXA3, EPHA3, SOX11, SLC26A8, CCRL1, FREM2, STOX2, ZNF479, LOC338862, ASTN2, FOLH1, SNX31, KREMEN1, ZNF479, ALS2CR11, FIGN, RORB, LOC732096, GYPA, ALPL, LHX2, GALNT5, SRD5A2L2, GALNT14, OVOL2, BMPR1B, UNC5B, ODZ2, ALPL, RASAL2, SHOX, C19orf59, ZNF114, SRGAP1, ELAVL2, NCRNA00032, LOC440345, FLJ30375, TFPI, PTGR1, ROBO1, NR2F2, GRM5, LUM, FLJ39051, COL1A2, CASP5, OPCML, TTC6, TFAP2B, CRISP2, SOX11, ANKRD30B, FLJ39051, SCN2A, MYNN, FOXA2, DKFZP434B061, LOC645323, SNIP, LOC645323, LOC374491, ADAM30, SIX3, FLJ36144, CARD8, KREMEN1, RP1-127L4.6, FAM149A, B3GAT2, SPOCK3, G30, ITGBL1, IQGAP3, C7orf45, ZNF608, LOC375010, LRP2, TGFB2, SHOX2, HOXC4/// HOXC6, ELTD1, FAM182B///RP13-401N8.2, PRO0478, LIFR, FOLH1, EHF, NDST3, BRUNOL5, LOC728460, PDE1A, POU2AF1, FAT1, PCDH11X///PCDH11Y, FLJ37786, SLC22A4, DHRS13, EHF, MEG3, PIWIL1, LOC203274, LOC100133920///LOC286297, DMRT1, ADM, VWA3B, GAFA3, HESX1, ADAMDEC1, CAV1, LAMB4, TPTE, PPP1R1C, HPSE, AIM2, RUNDC3B, CARD16, FAM124A, MGC39584, OSM, RFX2, MYBPC1, LTBR, C18orf2, SNRPN, FLJ36031, IL1B, TRPM1, OSTCL, MAPK14, KCNJ15///LOC100131955, FIGN, HNT, S100A12, CHIT1, C7orf53, FAM13A1, GNAO1, MAPK14, FAM55D, PRKD2, LIMK2, C18orf54, IGFBP5, EVI1, PLSCR1, FOXC1, LOC646627, ZNF462, CNTLN, ZNF438, DEFB105A///DEFB105B, LOC340017, C1orf67, ACSL1, ADH1B, SLC2A14///SLC2A3, IL1B, ST3GAL4, UBE2J1, PNPLA3 and PAPPA when compared to the control level, and/or a decrease in expression of a plurality of the following genes: NBPF10///RP11-94I2.2, SFXN1, SPIN3, UNC84A, OLFM2, PPM1K, P2RY10, ZNF512B, MORF4L2, GIGYF2, ERAP2, SLFN13, LOC401431, MED6, BAIAP2L1///LOC100128461, LNPEP, MBNL1, NOS3, MCF2L, KIAA1659, SCAMP5, LOC648921, ANAPC5, SPON1, FUS, GPR22, GAL3ST4, METTL3, LOC100131096, FAAH2, SMURF2, SNRPN, FBLN7, GLS, G3BP1, RCAN3, EPHX2, DIP2C, CCDC141, CLTC, FOSB, CACNA1I, UNQ6228, ATG9B, AK5, SPIN3, RBM14, SNRPN, MAN1C1, HELLS, EDAR, SLC3A1, ZNF519, LOC100130070///LOC100130775/// LOC100131787///LOC100131905///LOC100132291/// LOC100132488///RPS27, ZC3H12B, IQGAP2, SOX8, WHDC1L2, TNPO1, TNFRSF21, TSHZ2, DMRTC1/// DMRTC1B, GSTM1, GSTM2, PNMA6A, CAND1, CCND3, GSTM1, GUSBL2 when compared to the control level is a reference profile for a subject who has experienced or is at risk for transient ischemic attack.

The reference profiles can be entered into a database, e.g., a relational database comprising data fitted into predefined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. In one embodiment, the invention matches the experimental sample to a database of reference samples. The database is assembled with a plurality of different samples to be used as reference samples. An individual reference sample in one embodiment will be obtained from a patient during a visit to a medical professional. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status and one where the samples are grouped primarily by pharmacological status. Within each table the samples can be further grouped according to the two remaining categories. For example the physiological status table could be further categorized according to disease and pharmacological status.

As will be appreciated by one of skill in the art, the present invention may be embodied as a method, data processing system or program products. Accordingly, the present invention may take the form of data analysis systems, methods, analysis software, etc. Software written according to the present invention is to be stored in some form of computer readable medium, such as memory, harddrive, DVD ROM or CD ROM, or transmitted over a network, and executed by a processor. The present invention also provides a computer system for analyzing physiological states, levels of disease states and/or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input. Computer systems may be used to execute the software of an embodiment of the invention (see, e.g., U.S. Pat. No. 5,733,729).

8. Providing Appropriate Treatment and Prevention Regimes to Patient

Upon a positive determination or confirmation that a patient has experienced a stroke, and a determination of the cause of stroke, e.g., using the biomarkers provided herein, the methods further provide for the step of prescribing, providing or administering a regime for the prophylaxis or treatment of ischemic stroke or SDI. By diagnosing the occurrence and/or the cause of stroke using the biomarkers described herein, a patient can rapidly receive treatment that is tailored to and appropriate for the type of stroke that has been experienced, or that the patient is at risk of experiencing.

If the expression levels of the plurality of lacunar stroke-associated biomarkers indicate the occurrence or risk of lacunar stroke, a positive diagnosis of lacunar stroke can be supported or confirmed using methods known in the art. For example, the patient can be subject to clinical evaluation (e.g., determination of one or more of the lacunar syndromes, including (1) Pure motor stroke/hemiparesis, (2) Ataxic hemiparesis, (3) Dysarthria/clumsy hand, (4) Pure sensory stroke, and (5) Mixed sensorimotor stroke), radiologic imaging, retinal imaging, evaluation of blood-brain barrier permeability, evidence of microhemorrhage and blood endothelial markers (e.g., (homocysteine, intercellular adhesion molecule 1 (ICAM1), thrombomodulin (TM), tissue factor (TF) and tissue factor pathway inhibitor (TFPI); Hassan, et al., Brain (2003) 126(Pt 2):424-32; and Hassan, et al., Brain. (2004) 127(Pt 1):212-9). Upon a positive diagnosis of lacunar stroke, the patient may be administered tissue plasminogen activator within three hours of an ischemic event if the patient is without contraindications (i.e. a bleeding diathesis such as recent major surgery or cancer with brain metastases). High dose aspirin may be given within 48 hours of an ischemic event. For long term prevention of recurrence, medical regimens may be aimed towards correcting the underlying risk factors for lacunar infarcts such as hypertension, diabetes mellitus and cigarette smoking.

In cases where non-lacunar stroke is indicated, further evaluation to the cause of non-lacunar stroke can be performed.

For example, if the expression levels of the plurality of ischemic stroke-associated biomarkers indicate the occurrence or risk of ischemic stroke, a positive diagnosis of ischemic stroke can be supported or confirmed using methods known in the art. For example, the patient can be subject to MRI imaging of brain and vessels, additional blood tests, EKG, and/or echocardiogram.

If the expression levels of the plurality of biomarkers indicate the occurrence or risk of cardioembolic stroke, the patient can be prescribed or administered a regime of an anticoagulant. Exemplary anticoagulants include aspirin, heparin, warfarin, and dabigatran.

If the expression levels of the plurality of biomarkers indicate the occurrence or risk of carotid stenosis, the patient can be prescribed or administered a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use. Patients having a moderately or severely narrowed neck (carotid) artery, may require or benefit from carotid endarterectomy. This preventive surgery clears carotid arteries of fatty deposits (atherosclerotic plaques) to prevent a first or subsequent strokes. In some embodiments, the patient may require or benefit from carotid angioplasty, or stenting. Carotid angioplasty involves using a balloon-like device to open a clogged artery and placing a small wire tube (stent) into the artery to keep it open.

If the expression levels of the plurality of biomarkers indicate the occurrence or risk of atrial fibrillation, the patient can be prescribed a regime of an anti-coagulant (to prevent stroke) and/or a pharmacological agent to achieve rate control. Exemplary anticoagulants include aspirin, heparin, warfarin, and dabigatran. Exemplary rate control drugs include beta blockers (e.g., metoprolol, atenolol, bisoprolol), non-dihydropyridine calcium channel blockers (e.g., diltiazem or verapamil), and cardiac glycosides (e.g., digoxin).

If the expression levels of the plurality of biomarkers indicate the occurrence or risk of transient ischemic attacks (TIA), the patient can be prescribed a regime of medications and/or life-style adjustments (e.g., diet, exercise, stress) to minimize risk factors can be recommended, including reducing blood pressure and cholesterol levels, and controlling diabetes. Several medications to decrease the likelihood of a stroke after a transient ischemic attack. The medication selected will depend on the location, cause, severity and type of TIA, if TIA has occurred. For example, the patient may be prescribed a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use to prevent or reduce the risk of stroke in patients who have experienced TIA. In some embodiments, the patient may be prescribed a regime of an anticoagulant. Exemplary anticoagulants include aspirin, heparin, warfarin, and dabigatran. Patients having a moderately or severely narrowed neck (carotid) artery, may require or benefit from carotid endarterectomy to clear carotid arteries of fatty deposits (atherosclerotic plaques) before another TIA or stroke can occur. In some embodiments, the patient may require or benefit from carotid angioplasty, or stenting.

The present methods for determining whether a patient has experienced or has a predisposition to experience lacunar stroke can be confirmed, complemented by, and/or used in conjunction with diagnostic tests known in the art for diagnosing lacunar stroke. For example, the present methods can be performed in conjunction with additional diagnostic based on imaging or ultrasound techniques. In various embodiments, the present methods are performed in conjunction with one or more diagnostic tests selected from the group consisting of X-ray computed tomography (CT), magnetic resonance imaging (MRI) brain scanning, vascular imaging of the head and neck with doppler or magnetic resonance angiography (MRA), CT angiography (CTA), electrocardiogram (e.g., EKG or ECG), cardiac ultrasound and cardiac monitoring. In various embodiments, the patient is subjected to cardiac monitoring for at least 2 days, e.g., for 2-30 days or for 7-21 days, e.g., for 2, 5, 7, 10, 12, 14, 18, 20, 21, 25, 28, 30, or more days, as appropriate. An infarction located in a subcortical region of the brain is associated with or correlated with a diagnosis of lacunar stroke. An infarction located in a cortical region of the brain, e.g., in regions of the penetrating arteries, e.g., basal ganglia, thalamus, internal capsule, corona radiata and/or pons, is associated with or correlated with a diagnosis of non-lacunar stroke. In some embodiments, the size of the infarction is determined.

9. Solid Supports and Kits

The invention further provides, a solid support comprising a plurality of nucleic acid probes that hybridize to a plurality (e.g., two or more, or all) of the genes set forth in Tables 3 and 4, and optionally Table 1. For example, the solid support can be a microarray attached to a plurality of nucleic acid probes that hybridize to a plurality (e.g., two or more, or all) of the genes set forth in Tables 3 and 4, and optionally Table 1. In various embodiments, the solid supports are configured to exclude genes not associated with or useful to the diagnosis, prediction or confirmation of a lacunar stroke, or for stroke generally. For example, genes that are overexpressed or underexpressed less than 1.2-fold in subjects with lacunar stroke in comparison to a control level of expression can be excluded from the present solid supports. In some embodiments, genes that are overexpressed or underexpressed less than 1.2-fold in subjects with ischemic stroke, including lacunar stroke, cardioembolic stroke, atherothrombotic stroke, TIA, and stroke subsequent to atrial fibrillation, in comparison to a control level of expression can be excluded from the present solid supports. The solid support may optionally further comprise a plurality of nucleic acid probes that hybridize to a plurality (e.g., two or more, or all) of the genes useful for the diagnosis of ischemic stroke, cardioembolic stroke, carotid stenosis, and/or atrial fibrillation, as described herein. In various embodiments, the solid support comprises 1000 or fewer (e.g., 900, 800, 700, 600, 500 or fewer) nucleic acid probes that hybridize to a plurality of ischemia-associated genes, as described herein. The solid support may be a component in a kit.

The invention also provides kits for diagnosing ischemia or a predisposition for developing ischemia. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. The kits may comprise a plurality of nucleic acid probes that hybridize to a plurality (e.g., two or more, or all) of the genes set forth in Tables 3 and 4. In one embodiment, the kits comprise a plurality of nucleic acid probes that hybridize to a plurality of the genes set forth in Table 3. In one embodiment, the kits comprise a plurality of nucleic acid probes that hybridize to a plurality of the genes set forth in Table 4. In one embodiment, the kits further comprise a plurality of nucleic acid probes that hybridize to a plurality of the genes set useful for the diagnosis of ischemic stroke, cardioembolic stroke, carotid stenosis, atrial fibrillation, and/or transient ischemic attacks (TIA), as described herein. The probes may be immobilized on an array as described herein.

In addition, the kit can comprise appropriate buffers, salts and other reagents to facilitate amplification and/or detection reactions (e.g., primers, labels) for determining the expression levels of a plurality of the genes set forth in Tables 3 and 4. In one embodiment, the kit comprises appropriate buffers, salts and other reagents to facilitate amplification and/or detection reactions (e.g., primers, labels) for determining the expression levels of a plurality of the genes set forth in Table 3. In one embodiment, the kit comprises appropriate buffers, salts and other reagents to facilitate amplification and/or detection reactions (e.g., primers) for determining the expression levels of a plurality of the genes set forth in Table 4. In one embodiment, the kit further comprises appropriate buffers, salts and other reagents to facilitate amplification and/or detection reactions (e.g., primers) for determining the expression levels of a plurality of the genes useful for the diagnosis of ischemic stroke, cardioembolic stroke, carotid stenosis, atrial fibrillation, and/or transient ischemic attacks (TIA), as described herein. The kits can also include written instructions for the use of the kit.

In one embodiment, the kits comprise a plurality of antibodies that bind to a plurality of the biomarkers set forth in Tables 3 and 4. The kits may further comprise a plurality of antibodies that bind to a plurality of the biomarkers useful for the diagnosis of ischemic stroke, cardioembolic stroke, carotid stenosis, atrial fibrillation, and/or transient ischemic attacks (TIA), as described herein. The antibodies may or may not be immobilized on a solid support, e.g., an ELISA plate.

EXAMPLES

The following examples are offered to illustrate, but not to limit the claimed invention.

Example 1

Gene Expression Profiling to Distinguish Lacunar from Non-Lacunar Stroke

Materials and Methods

Study Patients.

Patients with SDI, strokes of arterial and cardioembolic etiology were enrolled from the University of California, Davis, and the University of California, San Francisco. Study protocol was approved by the institutional review board at each site and written informed consent was obtained from each patient. Standardized clinical evaluations were performed on all patients including medical history, brain imaging, Doppler, vascular angiography, electrocardiogram, echocardiogram and 24-48 hour cardiac monitoring. Blood samples were drawn into PAXgene tubes (PreAnalytiX, Hilden, Germany) within 72 hours of stroke onset for gene expression analysis.

The diagnosis of stroke was made by two board certified stroke neurologists. Lacunar stroke was defined by clinical symptoms consistent with a lacunar syndrome and evidence of restricted diffusion on MRI with a largest diameter <15 mm occurring in the basal ganglia, thalamus, internal capsule, corona radiata or pons. Patients with lacunar stroke did not have evidence of embolic source despite investigation, including no evidence of intracranial or extracranial stenosis >50% or a potential moderate to high risk cardioembolic source. Lacunar strokes with incomplete investigations were not included for study. SDI of unclear etiology were defined as infarction in the basal ganglia, thalamus, internal capsule, corona radiata or brainstem >15 mm in diameter or <15 mm with a potential cardioembolic or ipsilateral arterial cause of stroke. Non-lacunar strokes occurred had evidence of infarction on imaging non-lacunar stroke regions, and were of identified cardioembolic or arterial source. Cardioembolic strokes included patients with atrial fibrillation, acute myocardial infarction, valvular heart disease and marked ventricular hypokinesis with hemispheric infarcts. Patients with PFO, atrial myxoma or endocarditis were not included. Arterial strokes were defined as stenosis >50% of an extracranial or intracranial artery referable to the infarct without evidence of other cause of stroke. Differences between groups were analyzed using Fisher's exact test or two-tailed t-test where appropriate.

Sample Processing.

PAXgene tubes were used to collect a venous blood sample within 72 hours of stroke onset (PreAnalytiX, Germany). Samples were stored at −80° C. and processed at the same time in the same laboratory to reduce batch effect. Total RNA was isolated according to the manufacturer's protocol (PAXgene blood RNA kit; PreAnalytiX). RNA concentration was determined by Nano-Drop (Thermo Fisher) and RNA quality by Agilent 2100 Bioanalyzer. Samples required A260/A280 absorbance ratios of purified RNA ≥2.0 and 28S/18S rRNA ratios ≥1.8. Reverse transcription, amplification, and sample labeling were carried out using NuGEN's Ovation Whole Blood Solution (NuGEN Technologies, San Carlos, Calif.). Each RNA sample was hybridized according to the manufacturer's protocol on Affymetrix Human U133 Plus 2.0 GeneChips (Affymetrix Santa Clara, Calif.). Arrays were washed and processed on a Fluidics Station 450 and scanned on a Genechip Scanner 3000. Samples were randomly assigned to microarray batch stratified by stroke subtype.

Data Analysis.

Microarray data files were pre-processed using robust multichip averaging (RMA), mean-centering standardization and log 2 transformation. Partek Genomics Suite 6.4, Partek Inc., St. Louis, Mo.). Nonspecific interquartile range filtering was used to eliminate probesets with low variation (<0.5) across the dataset (Hackstadt and Hess, *BMC Bioinformatics* (2009) 10:11; Gentleman R., "Bioinformatics and computational biology solutions using R and Bioconductor," in *Statistics for biology and health*. New York: Springer Science+Business Media; 2005. p. xix, 473 pp.). Of the original 54697 probesets, 21526 passed this filtering step and were retained for further analysis. Probesets were further selected by the differences in gene expression between phenotypic classes of interest using Analysis of Covariance (ANCOVA), adjusted for age and gender with a false discovery rate ≤0.05 and fold change ≥|1.5| considered significant.

Classifier results were obtained using forward selection linear discriminant analysis with a multiple 10-fold cross-validation method comparing lacunar stroke to non-lacunar stroke. In each iteration, data were divided into 10 equal-sized subsamples. Nine of the subsamples were used to predict the cause of stroke in the remaining "left-out" subsample. This procedure was repeated 10 times, each time using a different left-out subsample, so that all patient samples were used to derive and evaluate predictors. Within each of the 10 folds of the cross-validation, the genes used in the classifier were reselected based only on the samples not left out, so that only the training set was used to derive predictors for the left-out subsample. Selected predictors represent genes whose expression is most stable within samples from the same phenotypic class (e.g. lacunar stroke) and whose expression differs the most between samples of a different class. Receiver operating characteristics were derived based on the instance probability of class membership and used to identify the optimal probability threshold to assign class membership to subjects of unknown stroke cause. The full classifier derived from subjects with known stroke subtype was further evaluated using a second validation cohort of subjects of known stroke cause. To predict the stroke subtype in patients with SDI of unclear cause, the full classifier was applied to the gene expression values and class membership assigned based on probability threshold determined from the training set. Logistic regression analyses were performed using Stata 10.1 (College Station, Tex., USA). Variables on univariate analysis with p≤0.2 were included in multivariate analysis. Results are reported as odds ratios (OR) with 95% confidence intervals.

Ingenuity Pathway Analysis (IPA, Ingenuity Systems®, on the internet at ingenuity.com) was used to identify the functional pathways associated with the 90 genes. This was done by testing whether the number of genes in a given pathway was greater than that expected by chance (p<0.05 considered significant using a Fisher's exact test).

Results

There were 116 subjects with ischemic stroke in the training cohort for this study. The mean age was 67 years (SD 10.7) and 54% were male. The cohort was ethnically mixed: 72 (62%) were Caucasian, 22 (19%) were African American, 7 (6%) were Hispanic, 7 (6%) were Asian, and 8 (7%) of other race. Demographic and clinical characteristics of subjects used in the training group for the comparison of lacunar stroke to non-lacunar stroke are shown in Table 2. There were 30 samples with lacunar stroke and 86 subjects with non-lacunar stroke (56 cardioembolic stroke, 30 arterial stroke). Age, NIHSS on admission, race, arterial source and cardiac source were significantly different between lacunar stroke and non-lacunar stroke patients (p<0.05).

TABLE 2

Demographic variables for patients with lacunar and non-lacunar ischemic stroke

| | Lacunar (n = 30) | Non-Lacunar (n = 86) | p-value |
|---|---|---|---|
| Age years (SD) | 61.1 (12.7) | 69.1 (12.7) | <0.001 |
| Race Caucasian n(%) | 12 (40.0%) | 60 (69.8%) | 0.005 |
| Gender Male n (%) | 13 (43.3%) | 55 (63.9%) | 0.056 |
| Adm-Temperature ° C. (SD) | 36.3 (0.5) | 36.4 (0.1) | 0.616 |
| Adm-NIHSS (SD) | 2.2 (2.9) | 10.2 (9.3) | <0.001 |
| Hypertension n(%) | 24 (80.0%) | 61 (70.9%) | 0.473 |
| Systolic BP mmHg (SD) | 163.2 (32.8) | 157.4 (28.2) | 0.358 |
| Diastolic BP mmHg (SD) | 87.6 (20.3) | 82.0 (18.1) | 0.156 |
| Diabetes n(%) | 13 (43.3%) | 24 (27.9%) | 0.171 |
| Weight kg (SD) | 79.4 (22.7) | 88.5 (19.8) | 0.376 |
| Hyperlipidemia n(%) | 13 (43.3%) | 40 (46.5%) | 0.647 |
| Atrial fibrillation n(%) | 0 (0%) | 25 (29.1%) | <0.001 |
| Cardiac Source | 0 (0%) | 56 (65.1%) | <0.001 |
| Arterial Source | 0 (0%) | 30 (34.9%) | <0.001 |
| Prior Stroke/TIA n(%) | 5 (16.7%) | 21 (24.4%) | 0.454 |
| Prior MI n(%) | 2 (6.7%) | 16 (18.6%) | 0.151 |
| CAGB n(%) | 1 (3.3%) | 14 (16.3%) | 0.111 |

Abbreviations: Adm, admission; BP, blood pressure; CABG, coronary artery bypass graft; MI, myocardial infarction; NIHSS, National Institutes of Health Stroke Scale.

Figure 2:
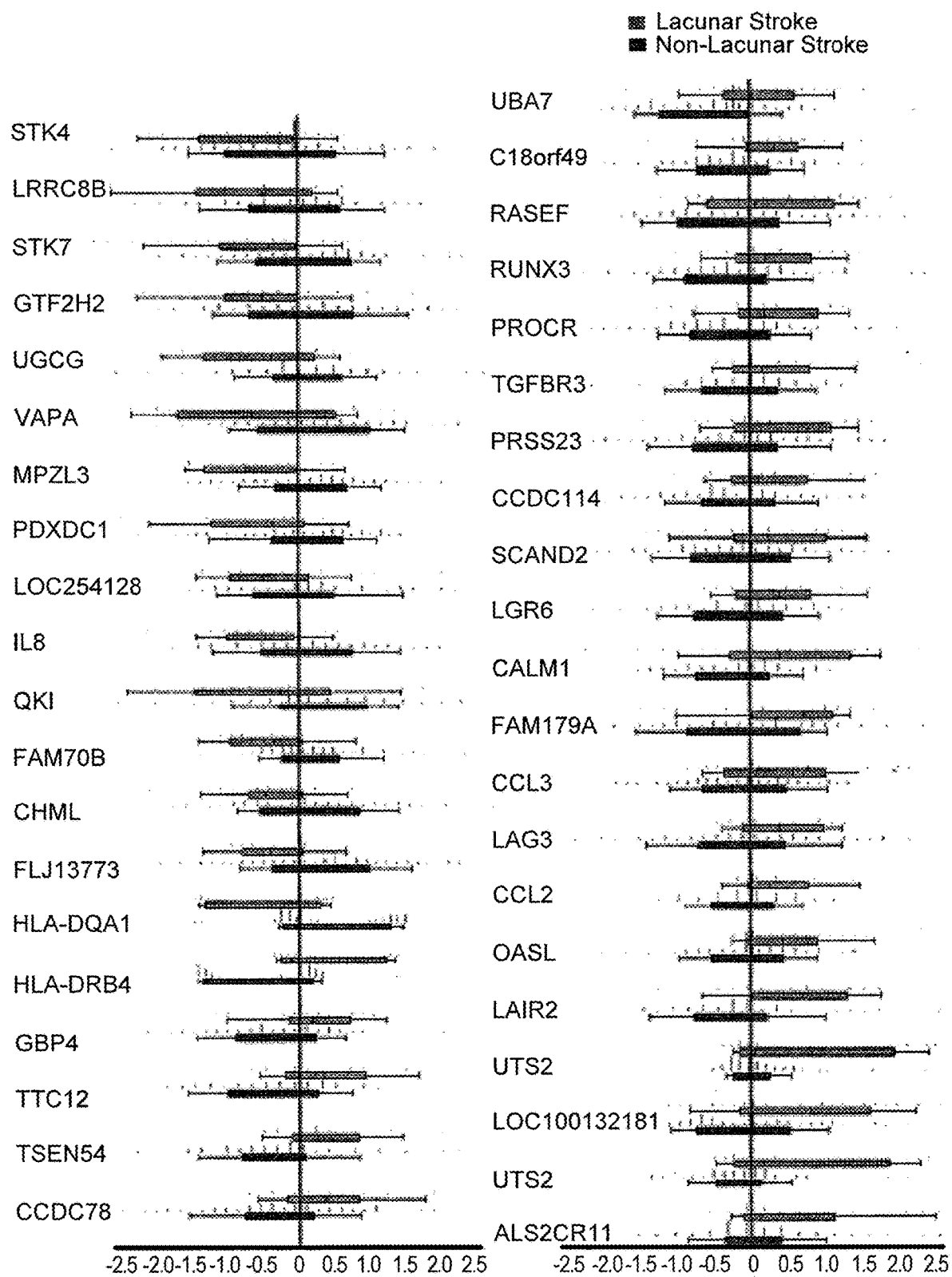
FIG. 2 illustrates box and whisker plots of the gene expression values for the 41 probesets that distinguished lacunar stroke from non-lacunar stroke. Lacunar stroke is shown in orange (upper plot), and non-lacunar stroke in green (lower plot). Each probeset demonstrates significant difference in gene expression between groups. However, no single probeset is able to completely separate every single patient with lacunar stroke from every patient with non-lacunar stroke. By combining information from multiple genes in the profile, the separation of lacunar from non-lacunar stroke is achieved for nearly all patients studied.
Figure 3:
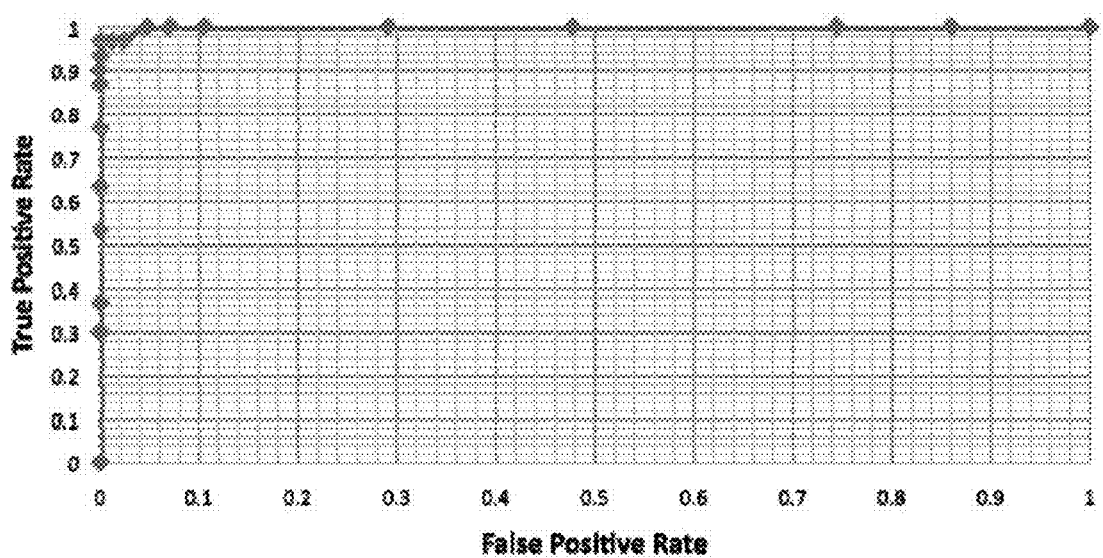
FIG. 3 illustrates a receiver operating characteristics (ROC) curve of the 41 probesets (40 genes) showing the sensitivity and specificity at various instance probabilities for the prediction of lacunar versus non-lacunar stroke.

A total of 96 probesets representing 90 genes were significantly different between lacunar and non-lacunar strokes (FDR<0.05 fold change >|1.5|) (Table 3). The 96 probesets were reduced to a list of 41 probesets (40 genes) using forward selection linear discriminant analysis (Table 4). A cluster plot and a plot of fold change for the 41 probesets that distinguish lacunar versus non-lacunar strokes are shown in FIG. 1. Detailed box plots of the mean centered expression values are shown in FIG. 2. A linear discriminant analysis model of the 41 probesets correctly distinguished lacunar from non-lacunar stroke in 97% of patients. Receiver Operating Characteristics curve was used to identify 0.7 as the optimal instance probability to discriminate between lacunar and non-lacunar stroke (true positive rate 0.97, false positive rate 0) (FIG. 3). Ten-fold cross-validation analysis was performed to evaluate prediction in the training set. The 41 probesets distinguished lacunar from non-lacunar stroke in 88% of patients ($^{22}/_{30}$ lacunar strokes; $^{80}/_{86}$ non-lacunar strokes) (FIG. 4).

TABLE 3

96 Probesets Representing 90 Genes Significantly Different Between Lacunar and Non-Lacunar Strokes

| Probeset ID | Gene Symbol | Gene Title | RefSeq Transcript ID | p-value (Lacunar vs. Non-Lacune) | Fold-Change (Lacunar vs. Non-Lacune) |
|---|---|---|---|---|---|
| 218091_at | AGFG1 | ArfGAP with FG repeats 1 | NM_001135187 /// NM_001135188 /// NM_001135189 /// NM_004504 | 0.00235784 | −1.50067 |
| 215483_at | AKAP9 | A kinase (PRKA) anchor protein (yotiao) 9 | NM_005751 /// NM_147185 | 0.00971715 | 1.579828 |
| 1553261_x_at | ALS2CR11 | amyotrophic lateral sclerosis 2 (juvenile) chromosome region, candidate 11 | NM_152525 | 0.00536689 | 1.59132 |
| 235723_at | BNC2 | basonuclin 2 | NM_017637 | 0.00937559 | 1.56652 |
| 1559975_at | BTG1 | B-cell translocation gene 1, anti-proliferative | NM_001731 | 0.00376377 | −1.53002 |
| 205839_s_at | BZRAP1 | benzodiazapine receptor (peripheral) associated protein 1 | NM_004758 /// NM_024418 | 0.006889 | 1.53193 |
| 232222_at | C18orf49 | chromosome 18 open reading frame 49 | — | 0.00266419 | 1.55196 |
| 213688_at | CALM1 | calmodulin 1 (phosphorylase kinase, delta) | NM_006888 | 0.00235943 | 1.61152 |
| 233157_x_at | CCDC114 | coiled-coil domain containing 114 | NM_144577 | 0.00154458 | 1.65214 |
| 236745_at | CCDC78 | coiled-coil domain containing 78 | NM_001031737 | 0.00537949 | 1.5279 |
| 216598_s_at | CCL2 | chemokine (C-C motif) ligand 2 | NM_002982 | 0.00400012 | 1.5258 |
| 205114_s_at | CCL3 /// CCL3L1 /// CCL3L3 | chemokine (C-C motif) ligand 3 /// chemokine (C-C motif) ligand 3-like 1 /// chemokine (C-C motif) ligand 3-like 3 | NM_001001437 /// NM_002983 /// NM_021006 | 0.00302906 | 1.51515 |
| 204103_at | CCL4 | chemokine (C-C motif) ligand 4 | NM_002984 | 0.00624874 | 1.54555 |
| 236588_at | CFDP1 | Craniofacial development protein 1 | NM_006324 | 0.00526084 | −1.53983 |
| 206079_at | CHML | choroideremia-like (Rab escort protein 2) | NM_001821 | 9.68E−05 | −1.83008 |
| 203921_at | CHST2 | carbohydrate (N-acetylglucosamine-6-O) sulfotransferase 2 | NM_004267 | 0.00531986 | 1.581 |
| 1557798_at | CNPY2 | Canopy 2 homolog (zebrafish) | NM_014255 | 0.00452098 | 1.52001 |
| 209716_at | CSF1 | colony stimulating factor 1 (macrophage) | NM_000757 /// NM_172210 /// NM_172211 /// NM_172212 | 0.000674827 | 1.7117 |
| 216836_s_at | ERBB2 | v-erb-b2 erythroblastic leukemia viral oncogene homolog 2, neuro/glioblastoma de | NM_001005862 /// NM_004448 | 0.00462673 | 1.62126 |
| 219694_at | FAM105A | family with sequence similarity 105, member A | NM_019018 | 0.00379549 | −1.50378 |
| 236717_at | FAM179A | family with sequence similarity 179, member A | NM_199280 | 0.00311876 | 1.6413 |
| 238226_at | FAM70B | family with sequence similarity 70, member B | NM_182614 | 0.00173252 | −1.51382 |
| 1559011_at | FLJ13773 | FLJ13773 | — | 0.000601925 | −1.76819 |
| 203178_at | GATM | glycine amidinotransferase (L-arginine:glycine amidinotransferase) | NM_001482 | 0.00359043 | −1.5849 |
| 235175_at | GBP4 | guanylate binding protein 4 | NM_052941 | 0.00445442 | 1.53211 |
| 235574_at | GBP4 | guanylate binding protein 4 | NM_052941 | 0.00465219 | 1.50933 |
| 212070_at | GPR56 | G protein-coupled receptor 56 | NM_001145770 /// NM_001145771 /// NM_001145772 /// NM_001145773 /// NM_001145774 | 0.00399735 | 1.61 |
| 238049_at | GRAMD3 | GRAM domain containing 3 | NM_001146319 /// NM_001146320 /// NM_001146321 /// NM_001146322 /// NM_023927 | 0.00914244 | 1.5714 |
| 219388_at | GRHL2 | grainyhead-like 2 (Drosophila) | NM_024915 | 0.00901445 | 1.59441 |
| 208365_s_at | GRK4 | G protein-coupled receptor kinase 4 | NM_001004056 /// NM_001004057 /// NM_182982 | 0.00677744 | 1.54491 |
| 223758_s_at | GTF2H2 | general transcription factor IIH, polypeptide 2, 44 kDa | NM_001515 | 0.00136485 | −1.70078 |
| 221540_x_at | GTF2H2 /// GTF2H2B /// GTF2H2C /// GTF2H2D | general transcription factor IIH, polypeptide 2, 44 kDa /// general transcription | NM_001042490 /// NM_001098728 /// NM_001098729 /// NM_001515 | 0.00365515 | −1.55919 |

TABLE 3-continued

96 Probesets Representing 90 Genes Significantly Different Between Lacunar and Non-Lacunar Strokes

| Probeset ID | Gene Symbol | Gene Title | RefSeq Transcript ID | p-value (Lacunar vs. Non-Lacune) | Fold-Change (Lacunar vs. Non-Lacune) |
|---|---|---|---|---|---|
| 203290_at | HLA-DQA1 | major histocompatibility complex, class II, DQ alpha 1 | NM_002122 | 2.54E−08 | −2.20603 |
| 209728_at | HLA-DRB4 | major histocompatibility complex, class II, DR beta 4 | NM_021983 /// XM_002346251 | 6.99E−06 | 1.91608 |
| 216318_at | IGHG1 | Immunoglobulin heavy constant gamma 1 (G1m marker) | — | 0.00296031 | −1.6144 |
| 207072_at | IL18RAP | interleukin 18 receptor accessory protein | NM_003853 | 0.00151018 | −1.52093 |
| 211506_s_at | IL8 | interleukin 8 | NM_000584 | 0.00463242 | −1.50845 |
| 242720_at | ITIH4 | inter-alpha (globulin) inhibitor H4 (plasma Kallikrein-sensitive glycoprotein) | NM_002218 | 0.0092498 | 1.56018 |
| 241347_at | KIAA1618 | KIAA1618 | NM_020954 | 0.00163972 | 1.59688 |
| 206486_at | LAG3 | lymphocyte-activation gene 3 | NM_002286 | 0.00815493 | 1.51228 |
| 207509_s_at | LAIR2 | leukocyte-associated immunoglobulin-like receptor 2 | NM_002288 /// NM_021270 | 0.00045044 | 1.81862 |
| 227819_at | LGR6 | leucine-rich repeat-containing G protein-coupled receptor 6 | NM_001017403 /// NM_001017404 /// NM_021636 | 0.000192318 | 1.80854 |
| 227835_at | LOC100132181 | Hypothetical protein LOC100132181 | — | 0.000335926 | 1.75913 |
| 1560830_a_at | LOC147646 | hypothetical protein LOC147646 | XM_001134195 /// XM_001134326 /// XM_001726058 | 0.000324794 | 1.60942 |
| 236739_at | LOC150622 | hypothetical LOC150622 | NR_026832 | 0.0077732 | 1.60267 |
| 211012_s_at | LOC161527 /// PML | hypothetical protein LOC161527 /// promyelocytic leukemia | NM_002675 /// NM_033238 /// NM_033239 /// NM_033240 /// NM_033244 /// NM_033246 | 0.0032518 | 1.54307 |
| 1557059_at | LOC254128 | Hypothetical protein LOC254128 | — | 0.00124615 | −1.62167 |
| 212978_at | LRRC8B | leucine rich repeat containing 8 family, member B | NM_001134476 /// NM_015350 | 0.00102493 | −1.65702 |
| 1570585_at | MPZL3 | myelin protein zero-like 3 | NM_198275 | 0.000173204 | −1.60248 |
| 231996_at | N4BP2 | NEDD4 binding protein 2 | NM_018177 | 0.00206464 | −1.58061 |
| 205660_at | OASL | 2′-5′-oligoadenylate synthetase-like | NM_003733 /// NM_198213 | 0.000308002 | 1.63843 |
| 210797_s_at | OASL | 2′-5′-oligoadenylate synthetase-like | NM_003733 /// NM_198213 | 0.000396146 | 1.62541 |
| 1555347_at | PDXDC1 | pyridoxal-dependent decarboxylase domain containing 1 | NM_015027 | 0.00077978 | −1.56922 |
| 232045_at | PHACTR1 | phosphatase and actin regulator 1 | NM_030948 | 0.00329088 | −1.59346 |
| 219566_at | PLEKHF1 | pleckstrin homology domain containing, family F (with FYVE domain) member 1 | NM_024310 | 0.000614903 | 1.75195 |
| 209282_at | PRKD2 | protein kinase D2 | NM_001079880 /// NM_001079881 /// NM_001079882 /// NM_016457 | 0.00358506 | 1.60351 |
| 203650_at | PROCR | protein C receptor, endothelial (EPCR) | NM_006404 | 0.00566754 | 1.56281 |
| 229441_at | PRSS23 | Protease, serine, 23 | NM_007173 | 0.00146505 | 1.69157 |
| 212262_at | QKI | quaking homolog, KH domain RNA binding (mouse) | NM_006775 /// NM_206853 /// NM_206854 /// NM_206855 | 0.00955483 | −1.53363 |
| 1553185_at | RASEF | RAS and EF-hand domain containing | NM_152573 | 0.00304521 | 1.68262 |
| 1553186_x_at | RASEF | RAS and EF-hand domain containing | NM_152573 | 0.00504628 | 1.65073 |
| 1554003_at | RGNEF | Rho-guanine nucleotide exchange factor | NM_001080479 | 0.00442102 | 1.50745 |
| 230469_at | RTKN2 | rhotekin 2 | NM_145307 | 0.00997383 | −1.51471 |
| 204197_s_at | RUNX3 | runt-related transcription factor 3 | NM_001031680 /// NM_004350 | 0.00898405 | 1.51341 |
| 206021_at | SCAND2 | SCAN domain containing 2 pseudogene | NR_003654 /// NR_004859 | 0.00891229 | 1.5413 |
| 223196_s_at | SESN2 | sestrin 2 | NM_031459 | 0.0054103 | 1.54604 |
| 222838_at | SLAMF7 | SLAM family member 7 | NM_021181 | 0.00335692 | 1.56069 |
| 202234_s_at | SLC16A1 | solute carrier family 16, member 1 (monocarboxylic acid transporter 1) | NM_003051 | 0.00459743 | −1.60487 |
| 210001_s_at | SOCS1 | suppressor of cytokine signaling 1 | NM_003745 | 0.00463398 | −1.51277 |
| 233516_s_at | SPAG17 | sperm associated antigen 17 | NM_206996 | 0.00242632 | −1.5873 |
| 218638_s_at | SPON2 | spondin 2, extracellular matrix protein | NM_001128325 /// NM_012445 | 0.00363533 | 1.59641 |
| 227725_at | ST6GALNAC1 | ST6 (alpha-N-acetyl-neuraminyl-2,3-beta-galactosyl-1,3)-N-acetylgalactosaminide | NM_018414 | 0.00587704 | −1.54288 |

TABLE 3-continued

96 Probesets Representing 90 Genes Significantly Different Between Lacunar and Non-Lacunar Strokes

| Probeset ID | Gene Symbol | Gene Title | RefSeq Transcript ID | p-value (Lacunar vs. Non-Lacune) | Fold-Change (Lacunar vs. Non-Lacune) |
|---|---|---|---|---|---|
| AFFX-HUMISGF3A/ M97935_MA_at | STAT1 | signal transducer and activator of transcription 1, 91 kDa | NM_007315 /// NM_139266 | 0.0096253 | 1.53095 |
| 243797_at | STK17B | serine/threonine kinase 17b | NM_004226 | 0.0015488 | −1.59518 |
| 1569791_at | STK4 | serine/threonine kinase 4 | NM_006282 | 0.00872568 | −1.53645 |
| 231294_at | STT3B | STT3, subunit of the oligosaccharyltransferase complex, homolog B (S. cerevisiae | NM_178862 | 0.00659319 | −1.55741 |
| 221499_s_at | STX16 | syntaxin 16 | NM_001001433 /// NM_001134772 /// NM_001134773 /// NM_003763 | 0.00402852 | −1.5285 |
| 212631_at | STX7 | syntaxin 7 | NM_003569 | 0.00132752 | −1.60106 |
| 210613_s_at | SYNGR1 | synaptogyrin 1 | NM_004711 /// NM_145731 /// NM_145738 /// | 0.00217283 | 1.51053 |
| 1557609_s_at | TBC1D12 | TBC1 domain family, member 12 | NM_015188 | 0.00719049 | −1.54224 |
| 220684_at | TBX21 | T-box 21 | NM_013351 | 0.00748882 | 1.53529 |
| 204731_at | TGFBR3 | transforming growth factor, beta receptor /// | NM_003243 | 0.00132619 | 1.68066 |
| 1569377_at | TMEM67 | transmembrane protein 67 | NM_001142301 /// NM_153704 /// NR_024522 | 0.00862787 | 1.52234 |
| 223384_s_at | TRIM4 | tripartite motif-containing 4 | NM_033017 /// NM_033091 | 0.00353022 | −1.56529 |
| 225879_at | TSEN54 | tRNA splicing endonuclease 54 homolog (S. cerevisiae) | NM_207346 | 0.00299112 | 1.52859 |
| 219587_at | TTC12 | tetratricopeptide repeat domain 12 | NM_017868 | 0.00822832 | 1.53053 |
| 230891_at | TUBE1 | Tubulin, epsilon 1 | NM_016262 | 0.00822258 | 1.57063 |
| 223279_s_at | UACA | uveal autoantigen with coiled-coil domains and ankyrin repeats | NM_001008224 /// NM_018003 | 0.00474228 | −1.55924 |
| 203281_s_at | UBA7 | ubiquitin-like modifier activating enzyme 7 | NM_003335 | 0.00155438 | 1.56379 |
| 221765_at | UGCG | UDP-glucose ceramide glucosyltransferase | NM_003358 | 0.00265623 | −1.61812 |
| 224967_at | UGCG | UDP-glucose ceramide glucosyltransferase | NM_003358 | 0.00349479 | −1.53463 |
| 220784_s_at | UTS2 | urotensin 2 | NM_006786 /// NM_021995 | 6.48E−05 | 1.73209 |
| 220785_at | UTS2 | urotensin 2 | NM_006786 /// NM_021995 | 0.000281237 | 1.55721 |
| 242780_at | VAPA | VAMP (vesicle-associated membrane protein)-associated protein A, 33 kDa | NM_003574 /// NM_194434 | 0.00827971 | −1.54802 |
| 1557450_s_at | WHAMML2 | WAS protein homolog associated with actin, golgi membranes and microtubules-like | NR_026589 | 0.00204599 | −1.61055 |
| 243618_s_at | ZNF827 | Zinc finger protein 827 | NM_178835 | 0.00743837 | 1.60401 |

TABLE 4

41 Probesets Using Forward Selection Linear Discriminant Analysis

| Probeset ID | Gene Symbol | Gene Title | RefSeq Transcript ID | p-value (Lacunar vs. Non-Lacune) | Fold-Change (Lacunar vs. Non-Lacune) |
|---|---|---|---|---|---|
| 1553261_x_at | ALS2CR11 | amyotrophic lateral sclerosis 2 (juvenile) chromosome region, candidate 11 | NM_152525 | 0.00536689 | 1.59132 |
| 232222_at | C18orf49 | chromosome 18 open reading frame 49 | — | 0.00266419 | 1.55196 |
| 213688_at | CALM1 | calmodulin 1 (phosphorylase kinase, delta) | NM_006888 | 0.00235943 | 1.61152 |
| 233157_x_at | CCDC114 | coiled-coil domain containing 114 | NM_144577 | 0.00154458 | 1.65214 |
| 236745_at | CCDC78 | coiled-coil domain containing 78 | NM_001031737 | 0.00537949 | 1.5279 |
| 216598_s_at | CCL2 | chemokine (C-C motif) ligand 2 | NM_002982 | 0.00400012 | 1.5258 |
| 205114_s_at | CCL3 /// CCL3L1 /// CCL3L3 | chemokine (C-C motif) ligand 3/// chemokine (C-C motif) ligand 3-like 1 /// chemokine (C-C motif) ligand 3-like 3 | NM_001001437 /// NM_002983 /// NM_021006 | 0.00302906 | 1.51515 |
| 206079_at | CHML | choroideremia-like (Rab escort protein 2) | NM_001821 | 9.68E−05 | −1.83008 |
| 236717_at | FAM179A | family with sequence similarity 179, member A | NM_199280 | 0.00311876 | 1.6413 |
| 238226_at | FAM70B | family with sequence similarity 70, member B | NM_182614 | 0.00173252 | −1.51382 |
| 1559011_at | FLJ13773 | FLJ13773 | — | 0.000601925 | −1.76819 |
| 235175_at | GBP4 | guanylate binding protein 4 | NM_052941 | 0.00445442 | 1.53211 |
| 223758_s_at | GTF2H2 | general transcription factor IIH, polypeptide 2, 44 kDa | NM_001515 | 0.00136485 | −1.70078 |

TABLE 4-continued

41 Probesets Using Forward Selection Linear Discriminant Analysis

| Probeset ID | Gene Symbol | Gene Title | RefSeq Transcript ID | p-value (Lacunar vs. Non-Lacune) | Fold-Change (Lacunar vs. Non-Lacune) |
|---|---|---|---|---|---|
| 203290_at | HLA-DQA1 | major histocompatibility complex, class II, DQ alpha 1 | NM_002122 | 2.54E−08 | −2.20603 |
| 209728_at | HLA-DRB4 | major histocompatibility complex, class II, DR beta 4 | NM_021983 /// XM_002346251 | 6.99E−06 | 1.91608 |
| 211506_s_at | IL8 | interleukin 8 | NM_000584 | 0.00463242 | −1.50845 |
| 206486_at | LAG3 | lymphocyte-activation gene 3 | NM_002286 | 0.00815493 | 1.51228 |
| 207509_s_at | LAIR2 | leukocyte-associated immunoglobulin-like receptor 2 | NM_002288 /// NM_021270 | 0.00045044 | 1.81862 |
| 227819_at | LGR6 | leucine-rich repeat-containing G protein-coupled receptor 6 | NM_001017403 /// NM_001017404 /// NM_021636 | 0.000192318 | 1.80854 |
| 227835_at | LOC100132181 | Hypothetical protein LOC100132181 | — | 0.000335926 | 1.75913 |
| 1557059_at | LOC254128 | Hypothetical protein LOC254128 | — | 0.00124615 | −1.62167 |
| 212978_at | LRRC8B | leucine rich repeat containing 8 family, member B | NM_001134476 /// NM_015350 | 0.00102493 | −1.65702 |
| 1570585_at | MPZL3 | myelin protein zero-like 3 | NM_198275 | 0.000173204 | −1.60248 |
| 205660_at | OASL | 2'-5'-oligoadenylate synthetase-like | NM_003733 /// NM_198213 | 0.000308002 | 1.63843 |
| 1555347_at | PDXDC1 | pyridoxal-dependent decarboxylase domain containing 1 | NM_015027 | 0.000777978 | −1.56922 |
| 203650_at | PROCR | protein C receptor, endothelial (EPCR) | NM_006404 | 0.00566754 | 1.56281 |
| 229441_at | PRSS23 | Protease, serine, 23 | NM_007173 | 0.00146505 | 1.69157 |
| 212262_at | QKI | quaking homolog, KH domain RNA binding (mouse) | NM_006775 /// NM_206853 /// NM_206854 /// NM_206855 | 0.00955483 | −1.53363 |
| 1553185_at | RASEF | RAS and EF-hand domain containing | NM_152573 | 0.00304521 | 1.68262 |
| 204197_s_at | RUNX3 | runt-related transcription factor 3 | NM_001031680 /// NM_004350 | 0.00898405 | 1.51341 |
| 206021_at | SCAND2 | SCAN domain containing 2 pseudogene | NR_003654 /// NR_004859 | 0.00891229 | 1.5413 |
| 1569791_at | STK4 | serine/threonine kinase 4 | NM_006282 | 0.00872568 | −1.53645 |
| 212631_at | STX7 | syntaxin 7 | NM_003569 | 0.00132752 | −1.60106 |
| 204731_at | TGFBR3 | transforming growth factor, beta receptor III | NM_003243 | 0.00132619 | 1.68066 |
| 225879_at | TSEN54 | tRNA splicing endonuclease 54 homolog (*S. cerevisiae*) | NM_207346 | 0.00299112 | 1.52859 |
| 219587_at | TTC12 | tetratricopeptide repeat domain 12 | NM_017868 | 0.00822832 | 1.53053 |
| 203281_s_at | UBA7 | ubiquitin-like modifier activating enzyme 7 | NM_003335 | 0.00155438 | 1.56379 |
| 221765_at | UGCG | UDP-glucose ceramide glucosyltransferase | NM_003358 | 0.00265623 | −1.61812 |
| 220784_s_at | UTS2 | urotensin 2 | NM_006786 /// NM_021995 | 6.48E−05 | 1.73209 |
| 220785_at | UTS2 | urotensin 2 | NM_006786 /// NM_021995 | 0.000281237 | 1.55721 |
| 242780_at | VAPA | VAMP (vesicle-associated membrane protein)-associated protein A, 3 3kDa | NM_003574 /// NM_194434 | 0.00827971 | −1.54802 |

The model derived from the training cohort was applied to a second validation test cohort of 36 ischemic stroke subjects of known non-lacunar etiology. The 41 probesets were able to correctly classify 35 of the 36 (98%) strokes as non-lacunar.

The model was applied to subjects with SDI of unclear cause (SDI >15 mm and SDI with possible embolic source). Of the 32 SDI patients, 15 were predicted to be of lacunar etiology and 17 were predicted to be of non-lacunar etiology.

To identify clinical features associated with the SDI of predicted lacunar etiology, univariate analysis was performed. SDI predicted to be lacunar were less likely to be of Caucasian race/ethnicity (OR 0.18, 0.04-0.86), less likely to have potential arterial source of stroke (OR 0.2, 0.04-0.9) and trended to have fewer potential cardiac source of stroke (OR 0.28, 0.04-1.69) (Table 5). The presence of hypertension and diabetes were not significantly increased in SDI predicted to be lacunar.

TABLE 5

Univariate logistic regression analysis of small deep infarcts (SDI) predicted to be lacunar (n = 15) compared to SDI predicted to be non-lacunar (n = 17)

| | Odds Ratio | 95% Conf Interval | p-value |
|---|---|---|---|
| Age years | 0.97 | 0.91-1.02 | 0.257 |
| Race Caucasian | 0.18 | 0.04-0.86 | 0.032 |
| Gender Male | 0.82 | 0.20-3.43 | 0.784 |
| Adm-Temperature ° C. | 0.99 | 0.97-1.03 | 0.960 |
| Adm-NIHSS | 0.92 | 0.71-1.19 | 0.522 |
| Hypertension | 0.87 | 0.11-7.04 | 0.894 |
| Systolic BP mmHg | 0.99 | 0.98-1.01 | 0.725 |
| Diastolic BP mmHg | 1.01 | 0.97-1.05 | 0.674 |
| Diabetes | 0.95 | 0.23-3.92 | 0.946 |
| Weight kg | 0.98 | 0.94-1.03 | 0.393 |
| Hyperlipidemia | 0.28 | 0.06-1.21 | 0.087 |
| Prior Stroke/TIA | 0.87 | 0.19-4.11 | 0.863 |
| Infarct Diameter | 1.06 | 0.98-1.15 | 0.122 |
| Striatocapsular location | 3.00 | 0.67-13.3 | 0.148 |
| ARWMC Score | 0.97 | 0.87-1.08 | 0.574 |
| Microhemorrhage | 0.20 | 0.02-2.02 | 0.171 |
| Arterial source (ipsilateral) | 0.20 | 0.04-0.90 | 0.037 |
| Cardiac source | 0.28 | 0.04-1.69 | 0.166 |
| Atrial Fibrillation | 0.33 | 0.03-3.61 | 0.366 |

Abbreviations: Adm, admission; ARWMC, Age Related White Matter Changes; BP, blood pressure; MI, myocardial infarction; NIHSS, National Institutes of Health Stroke Scale.

Multivariate logistic regression was performed to identify independent predictors of lacunar infarction. Independent predictors of SDI being of lacunar etiology were non-Caucasian race (OR 0.06, 0.005-0.60) and the absence arterial disease ipsilateral to the stroke (OR 0.06, 0.006-0.64). Table 6 shows the results of a multivariate stepwise logistic regression of all variables with p<0.2 on univariate analysis to identify independent predictors of lacunar stroke in small deep infarcts of unclear cause. Variables included in the model were arterial source, cardiac source, race Caucasian, striatocapsular location, infarct size, microhemorrhage and hyperlipidemia.

TABLE 6

| | OR | 95% Conf Interval | p-value |
|---|---|---|---|
| Arterial source (ipsilateral) | 0.056 | 0.006-0.64 | 0.019 |
| Race Caucasian | 0.063 | 0.005-0.60 | 0.017 |

Functional analysis of the 96 probesets revealed several pathways that were represented greater than expected by chance. The majority of pathways represented alterations in immune cells in the blood of patients with lacunar stroke. The top ten functional and canonical pathways are listed in Table 7, along with the genes expressed in these pathways. Table 7 shows a functional analysis of the 96 probesets (90 genes) that were different between lacunar and non-lacunar stroke. The top functional and canonical pathways that were represented greater than expected by chance (p<0.05, Fisher's exact test), along with the genes expressed in the listed pathways. The majority of pathways represent alterations in immune cells in the blood of patients with lacunar stroke that are different from non-lacunar stroke patients.

TABLE 7

| | Pathway | Genes | p-value |
|---|---|---|---|
| Canonical Pathways | Innate and Adaptive Immune Cell Communication | CCL3, CCL4, HLA-DRB4, IGHA1, IL8 | $4.8 \times 10^{-5}$ |
| | TREM1 Signaling | CCL2, CCL3, IL8 | $3.2 \times 10^{-3}$ |
| | T Helper Cell Differentiation | HLA-DQA1, STAT1, TBX21 | $4.9 \times 10^{-3}$ |
| | CCR5 Signaling in Macrophages | CALM1, CCL3, CCL4 | $5.6 \times 10^{-3}$ |
| | Role Macrophages, Fibroblasts and Endothelial Cells in Rheumatoid Arthritis | CALM1, CCL2, CSF1, IL8, IL18RAP, SOCS1 | $6.6 \times 10^{-3}$ |
| | Chemokine Signaling | CALM1, CCL2, CCL4 | $6.9 \times 10^{-3}$ |
| | Interferon Signaling | SOCS1, STAT1 | $1.3 \times 10^{-2}$ |
| | IL-6 Signaling | IL8, IL18RAP, SOCS1 | $1.5 \times 10^{-2}$ |
| | Antigen Presentation Pathways | HLA-DQA1, HLA-DRB4 | $1.5 \times 10^{-2}$ |
| Molecular Functions | Growth of Myeloid Cells & Leukocytes | CCL2, CCL3, CSF1, ERBB2, IL8, LAG3, PML, SOCS1 | $3.6 \times 10^{-9}$ |
| | Monocyte & Leukocyte Activation and Recruitment | CCL2, CCL3, CCL4, CSF1, HLA-DQA1, IL8, RUNX3, SPON2, STAT1, UTS2 | $1.9 \times 10^{-6}$ |
| | Immune Response | CCL2, CCL3, CCL4, CSF1, ERBB2, HLA-DQA1, HLA-DRB4, IL8, IL18RAP, LAG3, SOCS1, SPON2, STAT1, STK17B, TBX21, TGFBR3 | $2.2 \times 10^{-5}$ |
| | Cardiovascular process of blood vessel, endothelial adhesion | BTG1, CCL2, CCL3, IL8, PML, RUNX3, STK4, STX7, TGFBR3, UTS2 | $9.5 \times 10^{-4}$ |
| | Angiogenesis of endothelial cells | ERBB2, IL8 | $2.2 \times 10^{-3}$ |

To validate the method of gene selection and prediction model development, the entire process was repeated with gender as the outcome variable to be predicted. A profile of 41 distinct genes was derived in the training cohort that was significantly different between males and females (FDR≤0.05, fold change >|1.5|). A linear discriminant analysis model, built using these 41 genes, correctly predicted gender in all patients (86+30=116 out of 116 correct) on cross-validation analysis. The model was also evaluated on the validation set of 36 embolic subjects and the 30 SDI subjects, correctly predicting gender in all subjects (36/36 and 30/30). This shows that the methods used to derive and evaluate the outcome measure of lacunar stroke worked well and as expected.

DISCUSSION

The present study demonstrates that a gene expression profile can be used to distinguish patients with lacunar stroke from non-lacunar stroke. Further, when this gene expression profile is applied to patients with SDI of unclear cause (SDI>15 mm and SDI<15 mm with potential embolic sources), both lacunar and non-lacunar causes can be predicted. Clinical features associated with SDI of predicted lacunar etiology were non-Caucasian race and lack of arterial source. Given the difficulty in distinguishing lacunar from non-lacunar causes of SDI and the importance of this distinction in clinical management, developing a reliable expression profile for predicting or determining lacunar etiology finds clinical use.

Arterial Small Deep Infarcts

The presence of arterial disease ipsilateral to an SDI has been suggested as an indicator of non-lacunar infarction (Cupini, et al., *Stroke* (2002) 33(3):689-94; and Silvestrini, et al., *J Neurol.* (2006) 253(3):321-7). Patients with carotid or vertebral stenosis >50% ipsilateral to an SDI are often classified as a non-lacunar infarction. However, whether the arterial disease is the actual cause of the SDI or a coincidental disease occurring in a patient with symptomatic small vessel disease remains unclear (Devuyst and Bogousslaysky, *Stroke* (2003) 34(6):1409-11). Symptomatic carotid stenosis derives greater benefit from vascular intervention. Thus ascertaining whether the SDI is of lacunar or arterial etiology is of clinical significance. Furthermore, correct classification of stroke cause is important for clinical research of disease mechanism and the development of therapeutics.

Carotid endarterectomy in SDI patients with carotid stenosis does improve outcomes, supporting the argument that arterial disease is a cause of some SDI (Halliday, et al., *Lancet* (2010) 376(9746):1074-84; Lindley, et al., *Lancet Neurol.* (2009) 8(7):628-34). However, the benefit of endarterectomy in patients with SDI is less than for other stroke subtypes, potentially indicating that only a portion of SDI with carotid stenosis are truly symptomatic (Lindley, et al., supra). Other studies also suggest that arterial disease causes some SDI, with degree of vascular stenosis, intima medial thickness and arterial stiffness all having been reported as predictors of non-lacunar stroke (Jackson and Sudlow, *Brain* (2005) 128(Pt 11):2507-17; Lee, et al., *Stroke* (2005) 36(12):2583-8; Cupini, et al., *Stroke* (2002) 33(3):689-94; Silvestrini, et al., *J Neurol.* (2006) 253(3):321-7; Tuttolomondo, et al., *Atherosclerosis* (2010) 211(1):187-94; Jackson, et al. *Stroke* (2010) 41(4):624-9; Nah, et al., *Stroke* (2010) 41(12):2822-7; Cho, et al., *Eur Neurol.* (2010) 63(2):107-15; Mead, et al., *J Neurol Neurosurg Psychiatry* (1999) 67(5):682-4; Baumgartner, et al., *Stroke* (2003) 34(3):653-9; Bang, et al., *Arch Neurol.* (2004) 61(4):514-9; Kim, et al., *Eur Neurol.* (2010) 63(6):343-9; Bang, et al., *Arch Neurol.* (2002) 59(2):259-63). Additionally, Tejada, et al. reported a 7% absolute increase in ipsilateral compared to contralateral carotid stenosis in patients with SDI, suggesting carotid disease contributes to some SDI (Tejada, et al., *Stroke* (2003) 34(6):1404-9). However, this finding has not been demonstrated by others (Mead, et al., *J Neurol.* (2002) 249(3):266-71). Our study supports the notion that the presence of arterial disease is associated with non-lacunar infarction. Among the 32 patients with SDI of unclear cause, those predicted to have non-lacunar infarction were over five times more likely to have ipsilateral arterial disease.

Not all SDI with arterial disease were predicted to be of non-lacunar etiology. In 4 out of 12 SDI with arterial disease, a lacunar etiology was predicted. This suggests that some patients with SDI have asymptomatic arterial disease, coincidental to infarction. There were no clinical features recorded that were significantly different between SDI with arterial disease of predicted lacunar etiology compared to those of predicted non-lacunar etiology.

Cardioembolic Small Deep Infarcts

The presence of a cardiac source has also been suggested as a marker of non-lacunar SDI (Arboix, et al., *BMC Neurol.* (2010) 10:31; Jackson, et al. *Stroke* (2010) 41(4):624-9; Mead, et al., *J Neurol Neurosurg Psychiatry* (1999) 67(5):682-4; Jackson and Sudlow, *Stroke* (2005) 36(4):891-901; Bejot, et al., *Stroke* (2008) 39(7):1945-51; Lodder, et al., *Stroke* (1990) 21(3):375-81; Micheli, et al., *J Neurol.* (2008) 255(5):637-42; Jung, et al., *J Neurol Neurosurg Psychiatry.* (2001) 70(3):344-9; and Gouw, et al., *Stroke* (2008) 39(11):3083-5). In the present study, there was a trend for a cardiac source to be more common in SDI predicted to be of non-lacunar etiology, though statistically significant was not achieved. There were two subjects predicted to have lacunar stroke, one with atrial fibrillation and the other with cardiomyopathy. This suggests that some cardiac sources are coincidental to SDI, and some are probably causal. No clinical features were identified to be significantly different between SDI with a potential cardiac source of predicted lacunar versus non-lacunar etiology, though sample size was small.

Vascular Risk Factors, Race and Small Deep Infarcts

Vascular risk factor profiles are similar between lacunar and non-lacunar stroke (Jackson, et al. *Stroke* (2010) 41(4):624-9; Jackson and Sudlow, *Stroke* (2005) 36(4):891-901; Jackson and Sudlow, *Brain* (2005) 128(Pt 11):2507-17; and Bejot, et al., *Stroke* (2008) 39(7):1945-51). This is consistent with our study which did not identify hypertension or diabetes as being associated with a predicted diagnosis of lacunar infarction. However, non-Caucasian race/ethnicity was identified as being more common in SDI predicted to be of lacunar etiology. It is suggested that lacunar stroke occurs more frequently in non-Caucasians, including African American, Asian and Latino (Gross, et al., *Stroke* (1984) 15(2):249-55; Bamford, et al., *Stroke* (1987) 18(3):545-51; Bogousslaysky, et al., *Stroke* (1988) 19(9):1083-92; Huang, et al., *Stroke* (1990) 21(2):230-5, and Ohira, et al., *Stroke* (2006) 37(10):2493-8). Interestingly, non-Caucasian strokes also tend to have more intracranial atherosclerotic disease (Sacco, et al., *Stroke* (1997) 28(5):929-35; Sacco, *Stroke* (1995) 26(1):14-20; Gorelick, *Stroke* (1993) 24(12 Suppl):I16-9; discussion I20-1; Caplan, et al., *Stroke* (1986) 17(4):648-55). Whether race is an indicator of intracranial vascular disease not detected by angiography that is associated with lacunar stroke is an interesting possibility.

Lacunar Small Deep Infarcts

The diagnosis of lacunar stroke was made using clinical symptoms, imaging and ancillary investigation rule out other potential etiologies. Such features have been shown to make lacunar small vessel disease the most likely cause of a small deep infarct. This is indeed true in our study, where 22 out of 30 lacunar strokes were classified as lacunar on cross-validation analysis. However, there were 8 patients who met the criteria for lacunar stroke who were predicted to have a non-lacunar etiology based on their pattern of gene expression. Of interest none of these 8 patients had evidence of microhemorrhage on gradient echo recall MRI, whereas 6 of the 22 lacunar strokes of predicted lacunar etiology did (p=0.09). Though sample size in our study was small, the suggestion that microhemorrhages may be an important marker of lacunar stroke has previously been reported (Wardlaw, et al., *Stroke* (2006) 37(10):2633-6; Fan, et al., *J Neurol.* (2004) 251(5):537-41, Schonewille, et al., *J Stroke Cerebrovasc Dis.* (2005) 14(4):141-4). In future studies, more detailed analysis of small vessel disease markers including microhemorrhage, retinal imaging, blood brain barrier permeability and blood endothelial markers may provide better insight into features characteristic of lacunar stroke.

The identified differences in blood reflect immune differences between lacunar and embolic stroke, including differences in immune response to vascular risk factors. The genes identified as differentially expressed in lacunar stroke were over represented in canonical pathways involving innate and adaptive immune cell communication, TREM1 signaling, T-helper cell differentiation and immune cell signaling (Table 7). Over represented functional pathways included growth, activation and recruitment of leukocytes and myeloid cells, endothelial adhesion and angiogenesis. Specific inflammatory and/or genetic factors may predispose to endothelial damage. Indeed, others have identified markers of inflammation and endothelial dysfunction to be associated with lacunar strokes (Hassan, et al., *Brain* (2003) 126(Pt 2):424-32; van Iterson, et al., *BMC Bioinformatics* (2010) 11:450; Bevan, et al., *Stroke* (2008) 39(4):1109-14).

The present invention demonstrates that prediction of small deep infarcts of both lacunar and non-lacunar etiology. Further work-up of patients with SDI infarction can be performed to identify potential cardioembolic and arterial causes. Though clinical and imaging features may distinguish most lacunar strokes, there remains a group of SDI with non-lacunar etiologies that may require different management. Gene expression analysis shows promise as a powerful method to infer SDI etiology.

It is understood that the examples and embodiments described herein are for illustrative purposes only and that various modifications or changes in light thereof will be suggested to persons skilled in the art and are to be included within the spirit and purview of this application and scope of the appended claims. All publications, sequences of accession numbers, patents, and patent applications cited herein are hereby incorporated by reference in their entirety for all purposes.

What is claimed is:

1. A method for detecting the expression of a plurality of lacunar stroke-associated genes in a patient suffering from or at risk of experiencing lacunar stroke, the method comprising:
    a) determining a level of expression of the plurality of lacunar stroke-associated genes in a blood sample obtained from the patient,
    wherein the plurality of lacunar stroke-associated genes comprises RASEF, CALM1, TTC12, CCL3, CCL3L1, CCL3L3, CCDC78, PRSS23, LAIR2, C18orf49, UTS2, LGR6, PROCR, LAG3, OASL, LOC100132181, HLA-DRB4, CCL2, ALS2CR11, SCAND2, GBP4, RUNX3, TSEN54, UBA7, FAM179A, TGFBR3, and CCDC114; and
    (b) normalizing the level of expression of the plurality of lacunar stroke-associated genes to the expression level of a plurality of endogenous reference genes comprising USP7, MAPRE2, CSNK1G2, SAFB2, PRKAR2A, PI4KB, CRTC1, HADHA, MAP1LC3B, KAT5, GTSE1, CDC2L1, CDC2L2, TCF25, CHP, LRRC40, hCG_2003956, LYPLA2, LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445, LOC115110, and PEX16.

2. The method of claim 1, wherein the level of expression of the plurality of lacunar stroke-associated genes is concurrently or sequentially determined.

3. The method of claim 1, further comprising the step of obtaining the blood sample from the patient.

4. The method of claim 1, wherein the determining step is performed within 72 hours after a suspected ischemic event.

5. The method of claim 1, wherein the patient has at least one vascular risk factor.

6. The method of claim 1, wherein the patient shows evidence of microhemorrhage.

7. The method of claim 1, wherein the patient is non-Caucasian.

8. The method of claim 1, wherein the patient does not have arterial disease ipsilateral to the stroke.

9. The method of claim 1, wherein the level of expression of the plurality of lacunar stroke-associated genes is determined at the transcriptional level.

10. The method of claim 9, wherein the level of expression is determined by detecting hybridization of lacunar stroke-associated gene probes to gene transcripts of the plurality of lacunar stroke-associated genes in the blood sample.

11. The method of claim 10, wherein the hybridization step is performed on a nucleic acid array chip.

12. The method of claim 10, wherein the hybridization step is performed in a microfluidics assay plate.

13. The method of claim 9, wherein the level of expression is determined by amplification of gene transcripts of the plurality of lacunar stroke-associated genes.

14. The method of claim 13, wherein the amplification reaction is a polymerase chain reaction (PCR).

15. The method of claim 1, wherein the level of expression of the plurality of lacunar stroke-associated genes is determined at the protein level.

16. The method of claim 1, further comprising the step of determining the size and/or location of a suspected ischemic event.

* * * * *